(12) United States Patent
Fujiwara et al.

(10) Patent No.: US 7,566,306 B2
(45) Date of Patent: Jul. 28, 2009

(54) BIOLOGICAL INFORMATION PROCESSING APPARATUS AND OPERATION PROGRAM PRODUCT FOR THE SAME

(75) Inventors: Koji Fujiwara, Mishima-gun (JP);
Takanobu Ojima, Amagasaki (JP);
Toshio Norita, Mishima-gun (JP);
Yoshiroh Nagai, Nishinomiya (JP)

(73) Assignee: Konica Minolta Sensing, Inc.,
Sakai-Shi (JP)

( * ) Notice: Subject to any disclaimer, the term of this patent is extended or adjusted under 35 U.S.C. 154(b) by 269 days.

(21) Appl. No.: 11/224,813

(22) Filed: Sep. 13, 2005

(65) Prior Publication Data

US 2006/0229519 A1 Oct. 12, 2006

(30) Foreign Application Priority Data

Apr. 6, 2005 (JP) .............................. 2005-110278

(51) Int. Cl.
*A61B 5/00* (2006.01)
(52) U.S. Cl. ...................................... 600/485; 600/500
(58) Field of Classification Search ................. 600/300, 600/481, 483, 500
See application file for complete search history.

(56) References Cited

U.S. PATENT DOCUMENTS 5,941,837 A * 8/1999 Amano et al. ............... 600/595
6,023,662 A * 2/2000 Hayakawa et al. ............ 702/75
6,126,595 A * 10/2000 Amano et al. ................ 600/300
6,361,501 B1 * 3/2002 Amano et al. ................ 600/500
2003/0069490 A1 * 4/2003 Narimatsu ................... 600/407
2004/0106872 A1 * 6/2004 Kosuda ....................... 600/485

FOREIGN PATENT DOCUMENTS

| JP | 7-148126 A | 6/1995 |
| JP | 2002-65620 A | 3/2002 |
| JP | 2003-200031 A | 7/2003 |

OTHER PUBLICATIONS

Japanese "Notice of Reasons for Rejection", dated Sep. 4, 2007, for counterpart Japanese Patent Application No. 2005-110278; along with an English-language translation thereof.

* cited by examiner

*Primary Examiner*—Robert L Nasser
(74) *Attorney, Agent, or Firm*—Sidley Austin LLP

(57) ABSTRACT

A biological information processing apparatus is strong against the noises or disturbances, and can accurately determine an evaluation value or blood vessel age. A pulse wave acquirer acquires pulse wave information of a living body and a frequency analyzer analyzes a pulse wave frequency based on the pulse wave information obtained by the pulse wave acquirer. The characteristic value extractor extracts a characteristic value from pulse wave frequency information obtained by the analysis carried out by the frequency analyzer and a pulse wave property calculator calculates a pulse wave property or blood vessel age based on the characteristic value extracted by the characteristic value extractor.

16 Claims, 14 Drawing Sheets

BIOLOGICAL INFORMATION PROCESSING APPARATUS AND OPERATION PROGRAM PRODUCT FOR THE SAME

This application is based on patent application No. 2005-110278 filed in Japan, the contents of which are hereby incorporated by references.

BACKGROUND OF THE INVENTION

1. Field of the Invention

The present invention relates to a biological information processing apparatus for processing or measuring biological information regarding a living body, such as pulse wave, more particularly to a biological information processing apparatus capable of estimating the age of blood vessels, etc. from pulse wave information which is measured, and an operation program product for the processing apparatus.

2. Description of the Related Art

Conventionally, body weight, body fat, etc. are generally measured for health control purposes. Recently, the increasing health-consciousness of people causes a need to better understand the functional state of the circulatory system, especially the functional state of blood vessels and the blood flow, not just the blood pressure. In this respect, biological information processing apparatuses are known which are capable of measuring a photoelectric pulse wave by exposing a living body to red light and infrared light having different wavelengths and then measuring the light that has passed through (or reflected by) the living body owing to the fact, for example, that there is a difference in the respect of absorptive power between the hemoglobin and the oxygenated hemoglobin present in blood. Japanese Unexamined Patent Publication No. HEI5-200031 discloses the technology used in such biological information processing apparatus that calculates an estimated age of blood vessels by extracting, as characteristic points, a maximum value point and a minimum value point of an acceleration pulse wave which is obtained by taking the second derivative of a pulse wave.

However, the acceleration pulse wave has generally many noise components because it is obtained by taking the second derivative of the pulse wave. Also, the acceleration pulse wave is vulnerable to external disturbances because such point information as maximum value and minimum value is used as characteristic quantity as mentioned above. In other words, a slight variation occurring in the pulse wave (or acceleration pulse wave) causes a large error in the evaluation or deviated evaluation value which hinders the stable operation of the apparatus, and hinders the stable measurement and arithmetic processing. In order to avoid these problems, it is necessary to execute additional operations, for example, prolonged sampling, preprocessing such as filtering. Consequently, the conventional apparatuses unavoidably have the problems that the processing requires much longer time due to the complexity.

SUMMARY OF THE INVENTION

It is an object of the present invention to provide a biological information processing apparatus and an operation program product which are free from the problems residing in the prior art.

It is another object of the present invention to provide a biological information processing apparatus and an operation program product that can ensure stable operation and calculate an accurate evaluation value.

According to an aspect of the invention, information about a pulse wave of a living body is acquired. A frequency analyzer analyzes the frequency of the pulse wave based on the acquired pulse wave information. A characteristic value extractor extracts a characteristic value from the pulse wave frequency information obtained by the frequency analyzer. A pulse wave property calculator calculates a pulse wave property based on the characteristic value extracted by the characteristic value extractor.

These and other objects, features, aspects, and advantages of the present invention will become more apparent from the following detailed description of the preferred embodiments/examples with reference to the accompanying drawings.

DETAILED DESCRIPTION OF THE PREFERRED EMBODIMENTS OF THE INVENTION

Figure 1:
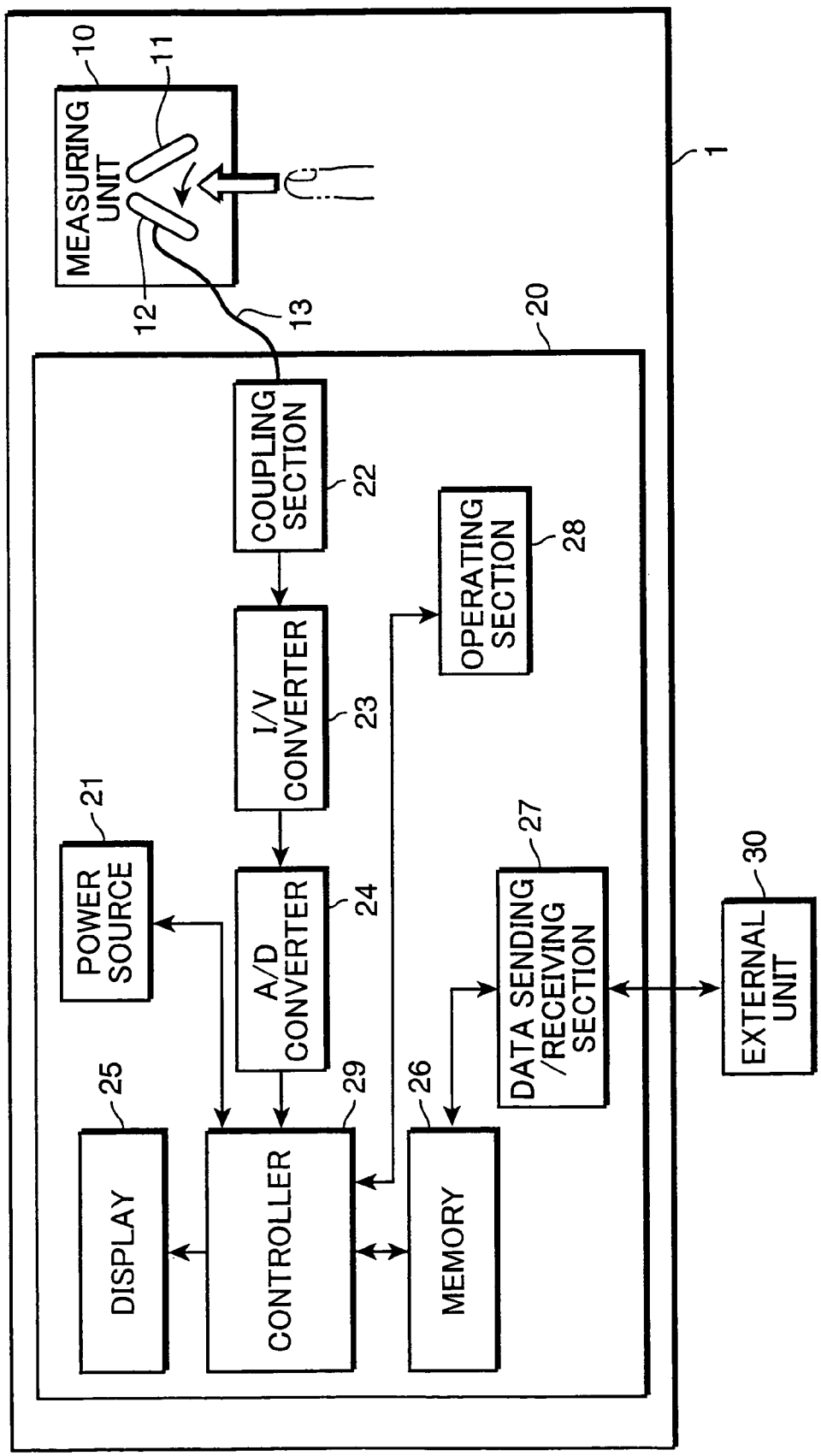
FIG. 1 is a block diagram showing a configuration of a biological information processing apparatus according to a first embodiment of the invention.

Referring to FIG. 1 showing a configuration of a biological information processing apparatus 1 according to a first embodiment of the invention, the biological information processing apparatus 1 comprises a measuring unit 10 which is to be attached to a living body to be measured to obtain biological information (i.e., pulse wave) from the living body, and a main body 20 as serving a main section of the measuring apparatus.

The measuring unit 10 includes a light emitter 11 and a light receiver 12. The light emitter 11 is a light source which alternately emits to the living body red light R having a wavelength λ1 in a red range and infrared light IR having a wavelength λ2 in the infrared range. The light source may be provided with, for instance, a light emitting diode (LED) capable of emitting red light R having a wavelength λ1 and infrared light IR having a wavelength λ2. Emission of red light R and infrared light IR from the light emitter 11 is controlled by a light controlling circuit provided in the measuring unit 10.

The light emitter 11 is constructed by a single LED to emit red light R and infrared light IR alternately. The light emitter 11 is not limited into such construction. It may be possible to adopt a construction that an LED emitting red light R having a wavelength λ1 and an LED emitting infrared light IR having a wavelength λ2, which are positioned on the same board and closer to each other. In this construction, the provision of the LED emitting red light R and the LED emitting infrared light IR on the same board and in proximity to each other makes it possible to measure two rays of light having two wavelengths which penetrates through or is reflected by the living body via an identical path.

The light receiver 12 includes a photoelectric element which generates a current in accordance with the intensity of the received light, and has sensitivity at least to the wavelength λ1 and the wavelength λ2, for example, silicon photo diode. The light receiver 12 is controlled by the light control circuit so as to synchronize with the light emission of the light emitter 11. The light receiver 12 photoelectrically converts the received light to an electrical signal in accordance with the light intensity, and outputs the signal to the main section 20.

The light emitter 11 and the light receiver 12 are held by a holding member (not illustrated) to keep them in a fixed position. The light emitter 11 and the light receiver 12 are arranged in such a way that the light receiver receives light having the wavelengths λ1, λ2 and having been passed through a part of the living body (LB) from the light emitter 11. The light emitter 11 and the light receiver 12 are arranged in such positions that the living body comes into a space between them. Specifically, an end of the light emitter 11 and an end of the light receiver 12 are pivotally combined to permit their respective other ends to pinch a part of the living body, e.g., a finger of the hand. However, the arrangement of the light emitter 11 and the light receiver 12 is not limited to this configuration, but may be modified to a configuration where a band is provided with the light emitter 11 and the light receiver 12, and wound around a part of the living body in such a way that the light emitter 11 and the light receiver 12 face each other.

Further, the light emitter 11 and the light receiver 12 are not necessarily placed in the opposing arrangement, and may be placed in a parallel arrangement where the light emitter 11 and the light receiver 12 face in the same direction. The light receiver 12 is coupled to the main section 20 via a connection cord or cable 13 which is a part of the measuring unit 10.

The measuring unit 10 carrying the light emitter 11 and the light receiver 12 is usually attached onto a finger of the hand or an ear lobe, and a back or wrist of the hand or a back of the foot in the case of infant in consideration of the facility in the attachment and the measurement to obtain data having a high SN (Signal-to-Noise) ratio.

Next, a general outline is given of the principle of measuring pulse waves using light from the light emitter 11 (light receiver 12) as described above. As is known, oxygen is carried to each cell of the living body by hemoglobin (Hb). Hemoglobin combines with oxygen in the lungs into oxygenated hemoglobin ($HbO_2$), then turns back to hemoglobin when the oxygen is used in the cell of the living body. The oxygen saturation ($SpO_2$) represents the proportion of oxygenated hemoglobin in the blood, and is determined by the following Equation (1) wherein CHb denotes the concentration of hemoglobin and $ChbO_2$ denotes the concentration of oxygenated hemoglobin.

Equation 1

$$SpO_2 = \frac{C_{HbO_2}}{C_{Hb} + C_{HbO_2}} \times 100\% \tag{1}$$

Figure 2:
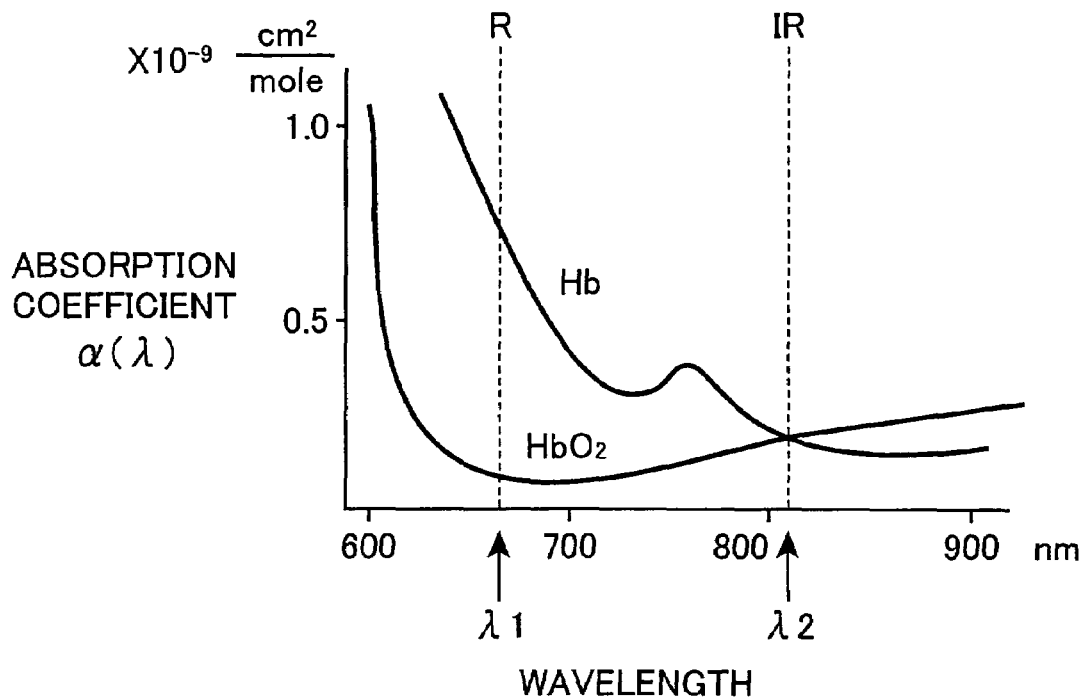
FIG. 2 is a graph showing light absorbance of hemoglobin and oxygenated hemoglobin.

On the other hand, the absorbance of hemoglobin and the absorbance of oxygenated hemoglobin depend on the light wavelength, and each absorption coefficient a (λ) has an absorption characteristic as shown in FIG. 2. The horizontal axis of the graph shown in FIG. 2 indicates the light wavelength in the unit of nm, whereas the vertical axis indicates the absorption coefficient in the unit of $\times 10^{-9}$ $cm^2$/mole. The hemoglobin and oxygenated hemoglobin have different absorption characteristics as shown in FIG. 2. The hemoglobin absorbs light more than the oxygenated hemoglobin with respect of the red light R in the red range but absorbs less than the oxygenated hemoglobin with respect to the infrared light IR in the infrared range. In the case where the red light R is made to have the wavelength λ1 of 660 nm in which the difference in the absorption coefficient between oxygenated hemoglobin and hemoglobin is largest and the infrared light IR is made to have the wavelength λ2 of 815 nm in which the difference in the absorption coefficient between oxygenated hemoglobin and hemoglobin is zero, specifically, the transmission amount of the red light R increases with the increase of hemoglobin and the transmission amount of the infrared light IR remains unchanged even if the ratio between oxygenated hemoglobin and hemoglobin changes. Accordingly, an oxygen saturation will be obtained by calculating a ratio between the transmission amount of the red light R and the transmission amount of the infrared light IR. Variations in the oxygen saturation have a relationship with variations in the blood amount or the amount of oxygenated hemoglobin which is fed to a measurement location in accordance with beatings or pulses of the heart. In other words, the oxygen saturation relates with the pulse wave. Owing to this fact, the biological information processing apparatus 1 can measure the pulse wave using the difference in the absorption characteristics of the hemoglobin and the oxygenated hemoglobin with respect to the red light R and the infrared light IR. However, it should be noted that in this embodiment, the pulse wave is measured indirectly using the difference in the absorption characteristics, but the pulse wave may also be measured directly using other methods.

Figure 3:
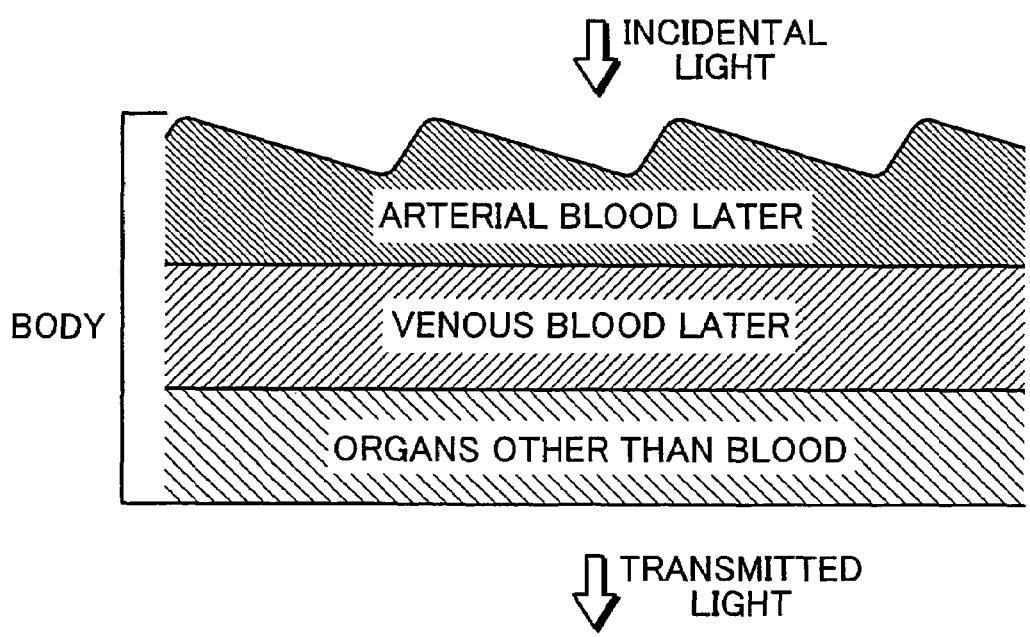
FIG. 3 is a diagram schematically showing an organic structure of a living body to describe light absorbance of the living body.

When the living body is exposed to irradiation of light, a part of the light is absorbed and another part of the light penetrates the living body. The living body has an arterial blood layer, a venous blood layer, and the other layers (organs other than the blood). The light absorption in the living body can be separated, as shown in FIG. 3, into absorption in the arterial blood layer, absorption in the venous blood layer, and absorption in the organs other than the arterial and venous blood layers. Since the venous blood layer and the organs other than the arterial and venous blood levels do not change in their structure with time, the light absorption in these portions is substantially constant. On the other hand, the arterial blood layer changes because the vessel diameter varies with the cardiac pulsation. Consequently, the absorption in the arterial blood layer or the transmittance in the arterial blood layer changes over time in accordance with pulses. The change in the intensity of transmitted light shows only information regarding the arterial blood layer, but does not show information regarding the venous blood layer and the organs other than the arterial and venous blood layers.

To compare variation ($\Delta I_R$ and $\Delta I_{IR}$) in the light amount of the red light R and the infrared light IR, it is necessary to remove or correct the difference between their incident amounts. However, it is very difficult to equalize the incident amounts ($I_0$) of the red light R and the infrared light IR to the living body. Even if they could be equalized, the comparison cannot be accomplished based on only variations ($\Delta I_R$ and $\Delta I_{IR}$) since the absorbance of each organ and venous blood differs with respect to red light R and infrared light IR. For this reason, the transmitted light amount ($I_R$) of red light R and the transmitted light amount ($I_{IR}$) of infrared light IR are normalized so that they are identical with each other, and the ratio between light amount variations, i.e., $(\Delta I_R/I_R)/(\Delta I_{IR}/I_{IR})$, of the venous blood is calculated to obtain an oxygen saturation. However, calculation of an oxygen saturation is not limited to this way and other various ways can be adopted.

The main section 20 includes an power source 21, a coupling section 22, an I/V converter 23, an A/D converter 24, a display 25, a memory 26, a data sending/receiving section 27, an operating section 28, and a controller 29. The power source 21, which includes an AC power or a battery, supplies electric power to each section of the biological information processing apparatus 1. The coupling section 22 includes a connector for electrically connecting the main section 20 with the distal end of the connection line 13 of the light receiver 12. The I/V converter 23 converts a current signal outputted by the light receiver 12 by the way of the coupling section 22 into a voltage signal, that is, executes an I/V conversion. The voltage signal obtained by the I/V converter 23 is outputted to the A/D converter 24 as a photoelectric pulse wave signal. The A/D converter 24 converts the inputted photoelectric pulse wave signal from an analog signal to a digital signal, that is, carries out an A/D conversion. The photoelectric pulse wave signal converted to the digital signal by the A/D conversion is outputted to the controller 29.

The display 25 displays data processed by the controller 29, and include a Liquid Crystal Display (LCD), a 7-segment LED, an organic photoluminescence display, a Cathode Ray Tube (CRT), a plasma display, or the like display device. The display 25 displays a variety of measurement information or biological information, such as pulse wave and oxygen saturation in a desired format.

The memory 26 stores a variety of setting data and calculation data provided by the controller 29, and includes an Electronically Erasable and Programmable Read Only Memory (EEPROM), a Static Random Access Memory (SRAM), Ferroelectric Random Access Memory (FeRAM), or the like storage device.

The data sending/receiving section 27 sends and receives information to and from an external unit 30 such as a Personal Computer (PC), and include a data sending/receiving device (or I/O interface) in accordance with wireless or wired transmission protocol, such as RS-232C, Universal Serial Bus (USB), Infrared Data Association (IrDA). The data sending/receiving section 27 may have a configuration to allow data stored in the memory 26 to be transferred or downloaded to an external unit 30 by the sending/receiving function. Also, the data may be transferred to an external unit 30 by wireless or wired transmission in a network such as LAN.

The operating section 28 includes a variety of switches or input buttons to input required operation instructions to operate each section of the apparatus. Specifically, the operating unit 28 has a power switch for turning on and off the power source 21, and a measurement switch for switching on and off to start and stop the detection of biological information, e.g., pulse length data, by the measuring unit 10 and the calculation based on the detection, and the like. Each switch is constructed in a structure of a push button which is mechanically pressed down, or a touch button provided in a crystal liquid display, or other suitable structure.

Figure 4:
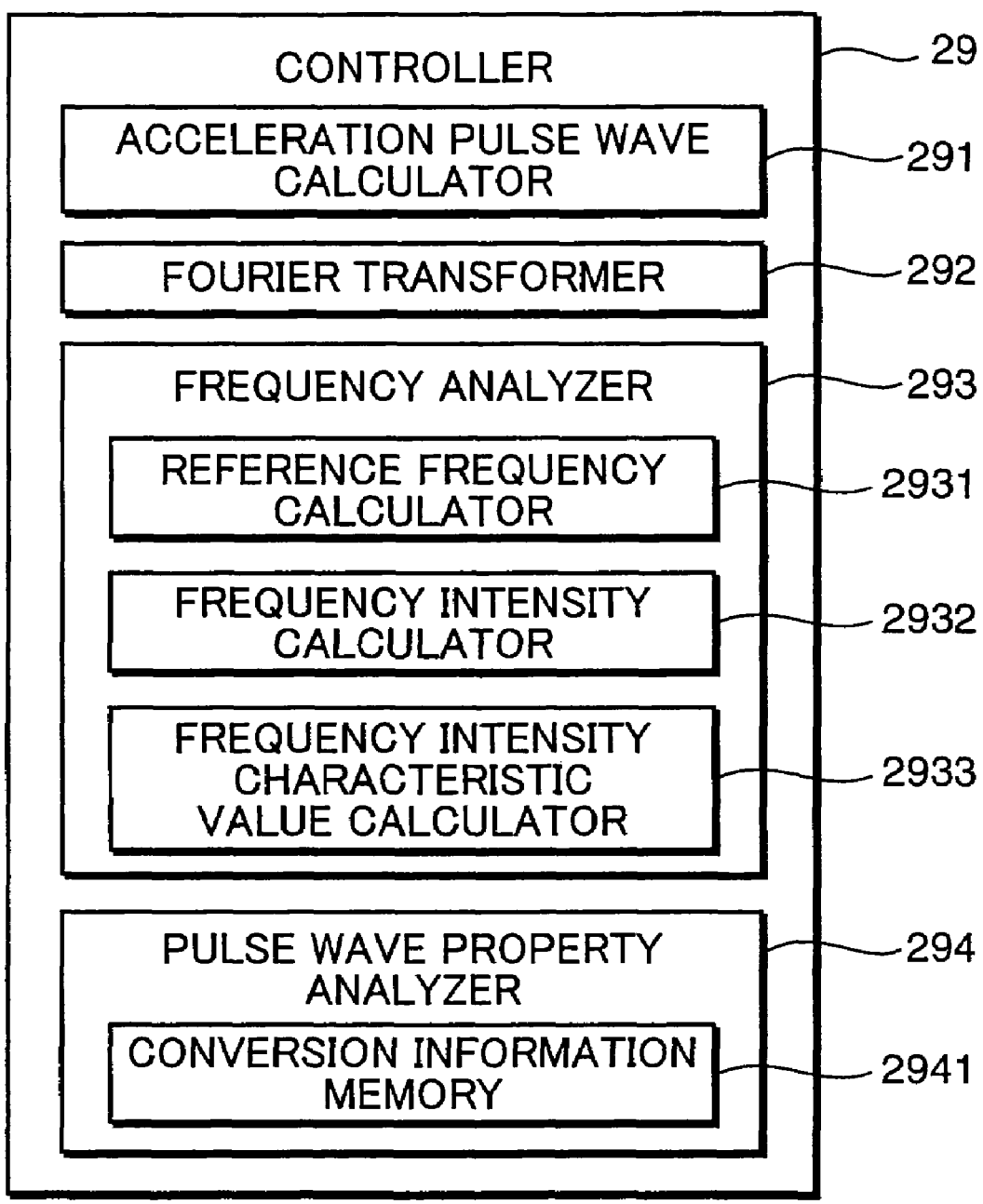
FIG. 4 is a block diagram showing functions of a controller provided in the biological information processing apparatus shown in FIG. 1.

The controller 29 includes a ROM for storing control programs and the like, a RAM for temporarily storing data, and a Central Processing Unit (CPU) for centrally executing necessary processing in accordance with programs read from the ROM and a Digital Signal Processor (DSP), and controls the entire operations of the biological information processing apparatus 1. Based on the data and programs stored in the ROM and RAM, the controller 29 carries out a calculation of calculating a frequency intensity characteristic value to be described later from a photoelectric pulse wave signal inputted thereto, and a calculation of calculating an estimated blood vessel age (hereinafter, referred to as vessel age) from the calculated frequency intensity characteristic value. However, it may be needless to say that not only vessel age but also oxygen saturation, pulse rate and the like are calculated. FIG. 4 is a block diagram illustrating functions of the controller 29. As shown in this figure, the controller 29 is provided with an acceleration pulse wave calculator 291, a Fourier transformer 292, a frequency analyzer 293, and a pulse wave property analyzer 294.

The acceleration pulse wave calculator 291 calculates an acceleration pulse wave from a pulse wave obtained by the measurement of the living body through the measuring unit 10. The acceleration pulse wave (acceleration pulse wave signal, acceleration pulse wave waveform) is calculated by taking the second derivative of the pulse wave (pulse wave waveform). Such acceleration pulse wave generally has a waveform shown in FIG. 5, more specifically, the waveform having a repetitive waveform pattern 503 which includes a large waveform indicated at 501, followed by a group of small waveforms indicated at 502. The large waveform indicated at 501 generates each timing of beat, and the duration of the waveform pattern 503 thus corresponds to the pulse wave of one beat. However, it should be noted that the pulse wave does not always have the same waveform pattern that is regularly repeated without any change, but it changes in time, in other words, the amplitude (height) and the phase of one pulse wave differs from another pulse wave, that is, the duration of the pulse wave of one beat changes. There is the possibility that no pulse wave is obtained due to a discontinuity in the detection of pulses.

Figure 5:
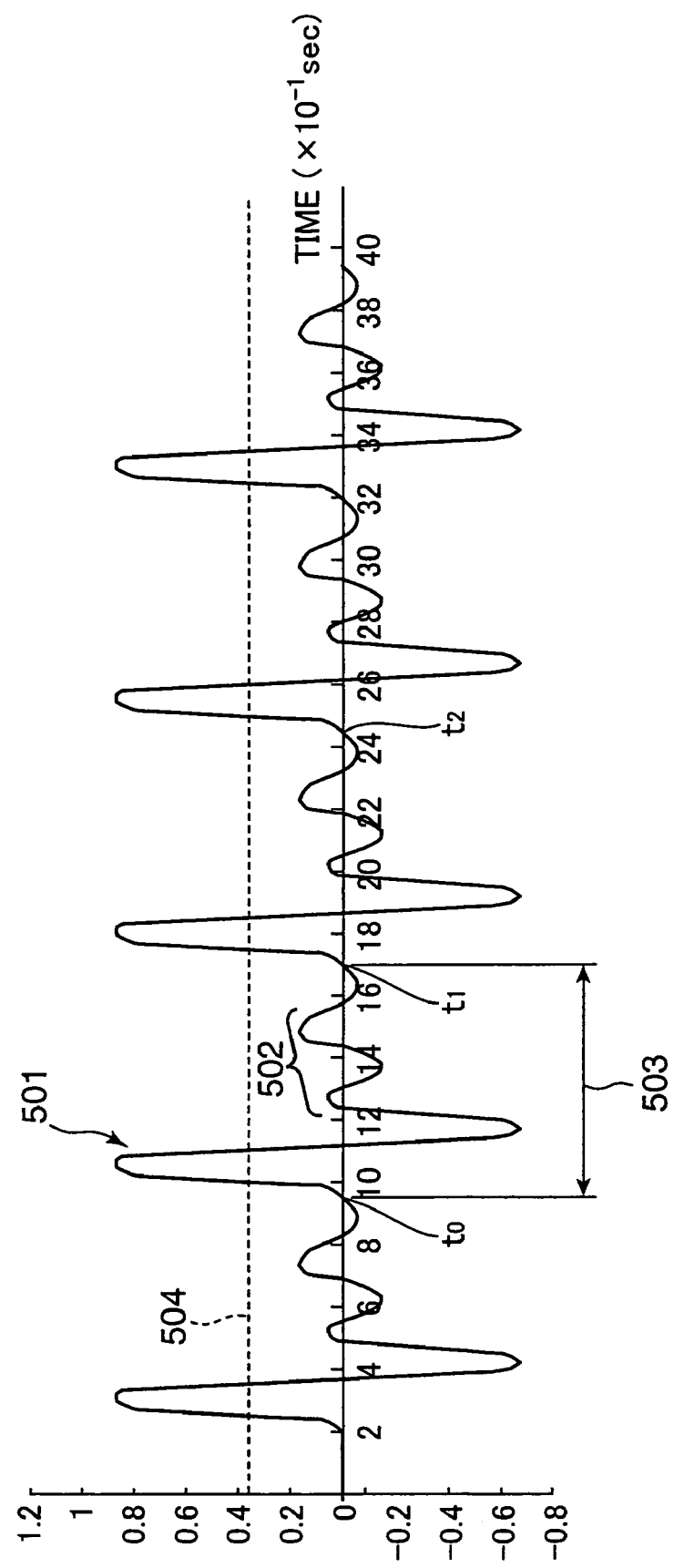
FIG. 5 is a graph showing an acceleration pulse wave.

The acceleration pulse wave calculator 291 detects or calculates a part acceleration pulse wave for one beat from the acceleration pulse wave which has been calculated. More specifically, as shown in FIG. 5, the acceleration pulse wave calculator 291 detects zero points ($t_0, t_1, t_2, \ldots$) right before exceeding a predetermined threshold 504 in the acceleration pulse wave signal, and then detects the section of the acceleration pulse wave signal that is in a duration ($t_i$-$t_{i+1}$) from one zero point to the next zero point as a part acceleration pulse wave for one beat. The detection of a part acceleration pulse wave for one beat is carried out because: 1) In the case where the pulse wave for a plurality of beats is detected for a long period of time, a peak of the pulse wave is likely to separate into a plurality of small peaks when the pulse wave greatly changes in time, resulting in damaged data; and 2) Thus, such damaged data should be avoided to ensure accuracy in the following calculations. The pulse wave detection for the minimum period of one pulse beat can avoid this problem. Also, detection of pulse wave for one beat may be carried out by a manner other than the above-mentioned manner.

Figure 6:
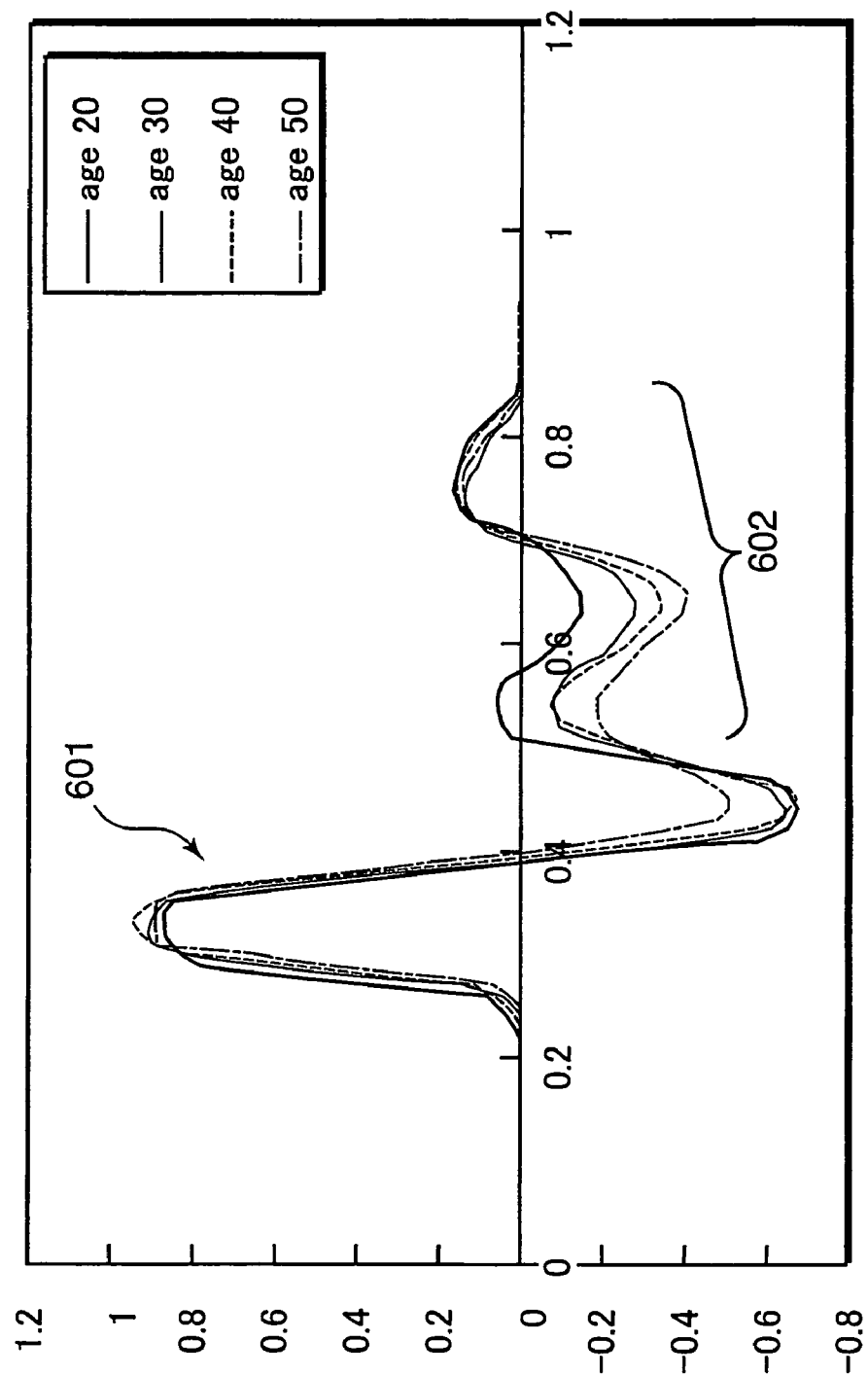
FIG. 6 is a graph showing acceleration pulse waves of different ages in one pulse beat.

The pulse wave is known to change its waveform depending on age. In the one cycle indicated at 503 in FIG. 5, specifically, the waveform changes according to the age of twenties, thirties, forties, and fifties as shown in FIG. 6. It will be seen that the fluctuation becomes smaller with an increase in the age. In other words, the fluctuations indicated at 602 following the great fluctuation indicated at 601 corresponding to one beat flattens in the increased age. The pulse wave relates with the amount of blood flowing through the blood vessel (arteries) as described above, but the waveform differences according to ages can be considered as showing the age of the blood vessel (hereinafter, referred to as vessel age). In other words, the elasticity of the blood vessel (hereinafter, referred to as vessel elasticity) decreases with an increase in the age, or the vessel hardens and the contraction rate of the vessel decreases with an increasing age, which consequently causes dull response to the beat represented by the fluctuation 602 and makes these waveform differences. However, it should be noted that the waveform differences are caused not only by variations in the vessel elasticity but also by deposits of cholesterol inside the blood vessel or other factors. Further, the pulse wave can be considered to include information not only about the blood vessel but also about the heart pumping the blood, but this specification refers to the vessel age only.

The Fourier transformer 292 carries out a Fourier transform (discrete Fourier transform) of each signal of part acceleration pulse waves (N in the number) continuous with one another having each the duration $(t_i-t_{i+1})$, and calculates a frequency intensity distribution for each part acceleration pulse wave. FIGS. 7 to 10 show examples of frequency intensity distribution for ages, respectively show vessel ages (standard vessel ages) of twenties, thirties, forties, and fifties. The graph at the right side of each of FIGS. 7 to 10 represents a pulse wave for a number of beats, the vertical axis showing the signal intensity, and the horizontal axis showing the time. The graph at the left side of each of FIGS. 7 to 10 represents a frequency intensity distribution or power spectrum which is obtained by taking a discrete Fourier transform of a standard waveform which is a pulse part of the pulse wave shown in the graph at the right side, the vertical axis showing the signal intensity, and the horizontal axis showing the frequency. These frequency intensity distributions show averaged frequency intensity distribution patterns for each age.

In the power spectrum of frequency intensity distribution shown in FIGS. 7 to 10, it will be seen that there are four large peaks. These peaks, i.e., the 0-th to third peaks, have the 0-th reference frequency, the first reference frequency, the second reference frequency, and third reference frequency, which are in the order of being greater. The 0-th peak (0-th reference frequency) corresponds to the pulse for actual one beat or the pulse motion (it is not a pulse wave caused by the response). Comparing the frequency intensity distribution shown in each figure, it can be understood that with an increase in age, the second peak (second reference frequency) tends to lower considerably, in other words, there is a correlation between the age and the frequency intensity distribution (each peak). Accordingly, it will be seen that a vessel age can be estimated from the pulse wave information based on these correlations (the lowering of the second peak). However, because the intensity (height of the peak) varies for each pulse, normalization is required as described later. In this embodiment, specifically, the second reference frequency (intensity) is normalized with the first reference frequency (intensity) to remove the influence of the variation and then estimate a vessel age.

The frequency analyzer 293 analyzes information about the frequency intensity distribution for each pulse calculated by the Fourier transformer 292 to thereby calculate a characteristic value (hereinafter, referred to as frequency intensity characteristic value) relating to each frequency intensity of the frequency intensity distribution. The frequency analyzer 293 comprises a reference frequency calculator 2931, a frequency intensity calculator 2932 and a frequency characteristic value calculator 2933.

Figure 7:
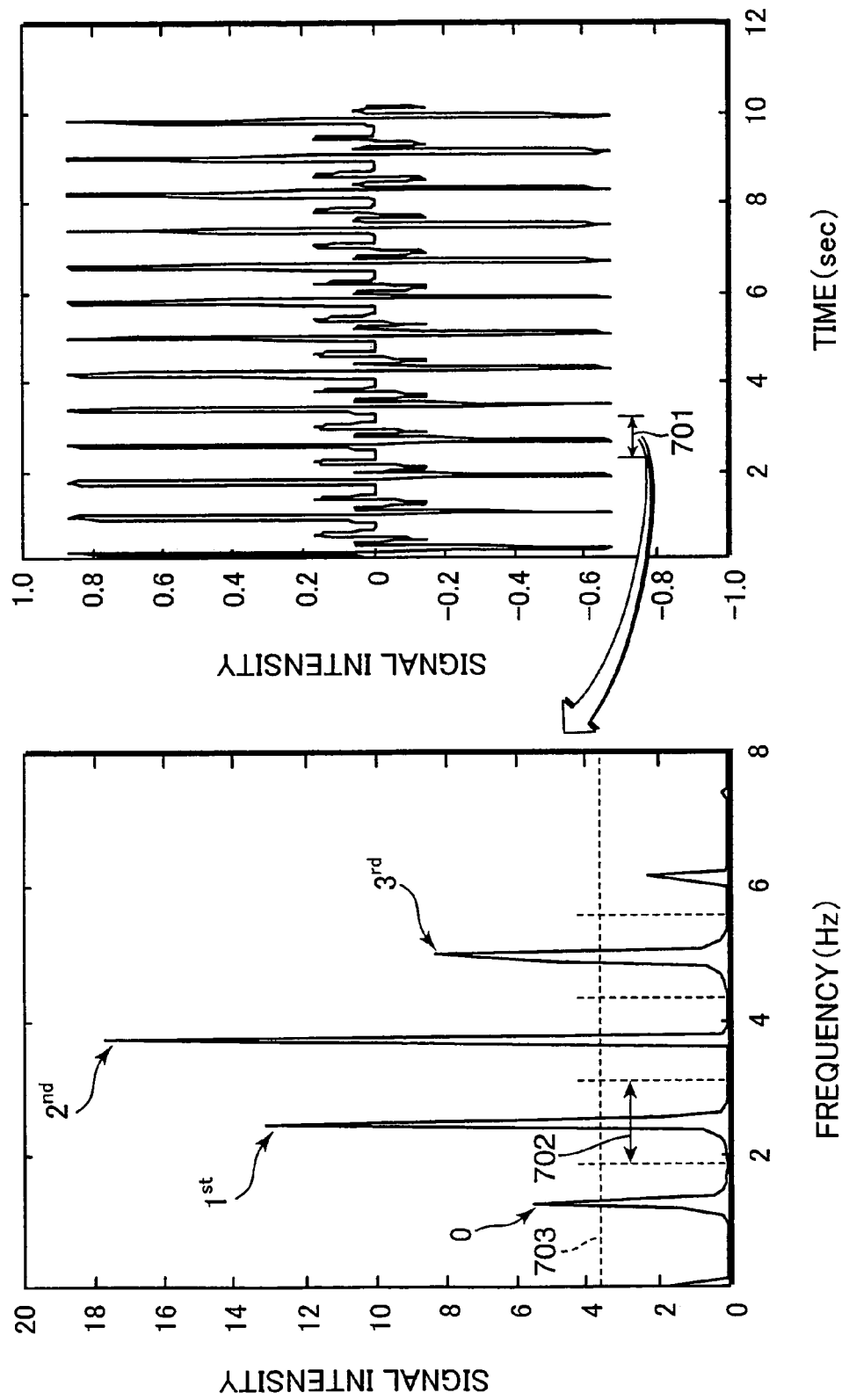
FIG. 7 is a graph showing an exemplary frequency intensity distribution of the age of twenties.
Figure 8:
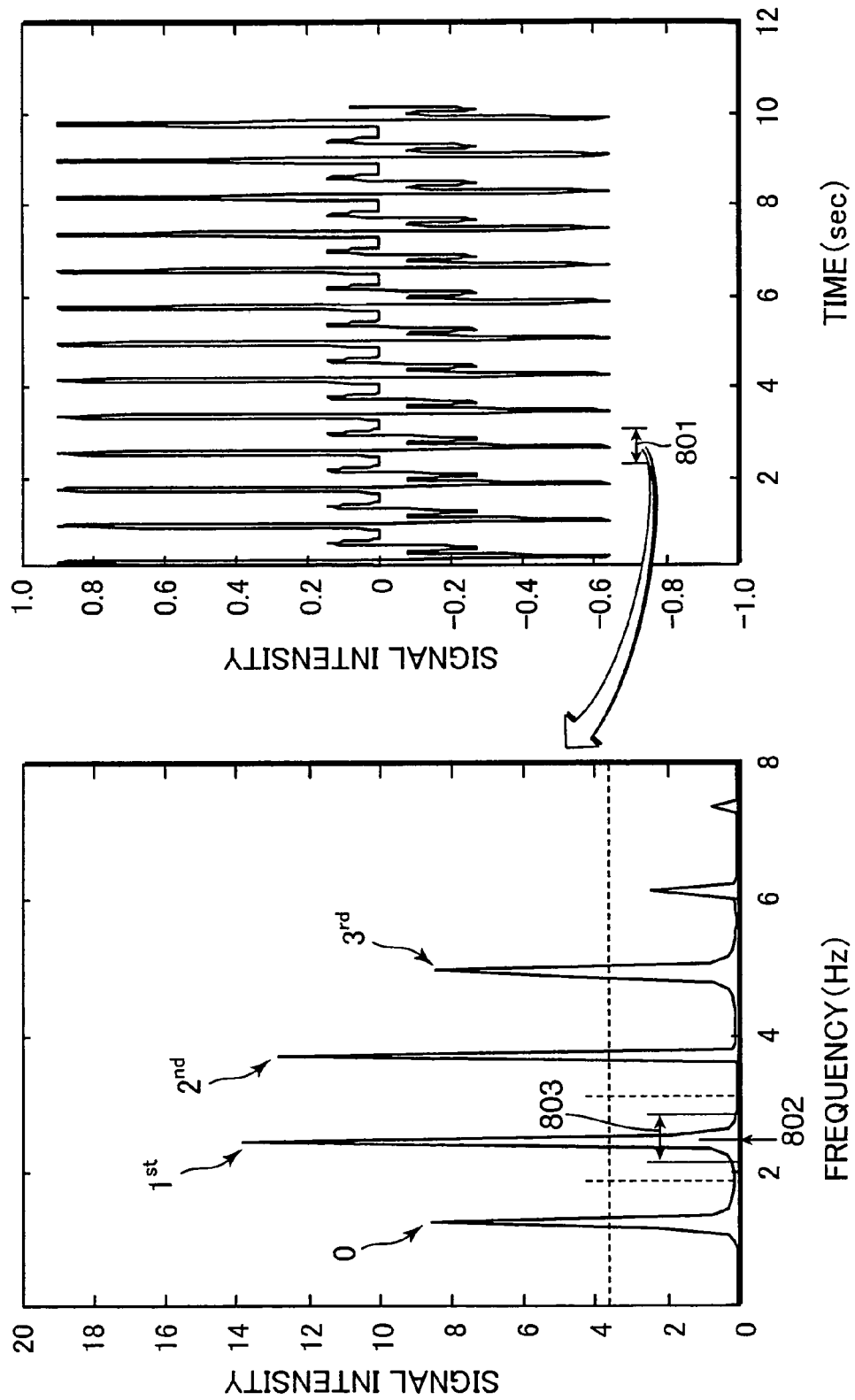
FIG. 8 is a graph showing an exemplary frequency intensity distribution of the age of thirties.
Figure 9:
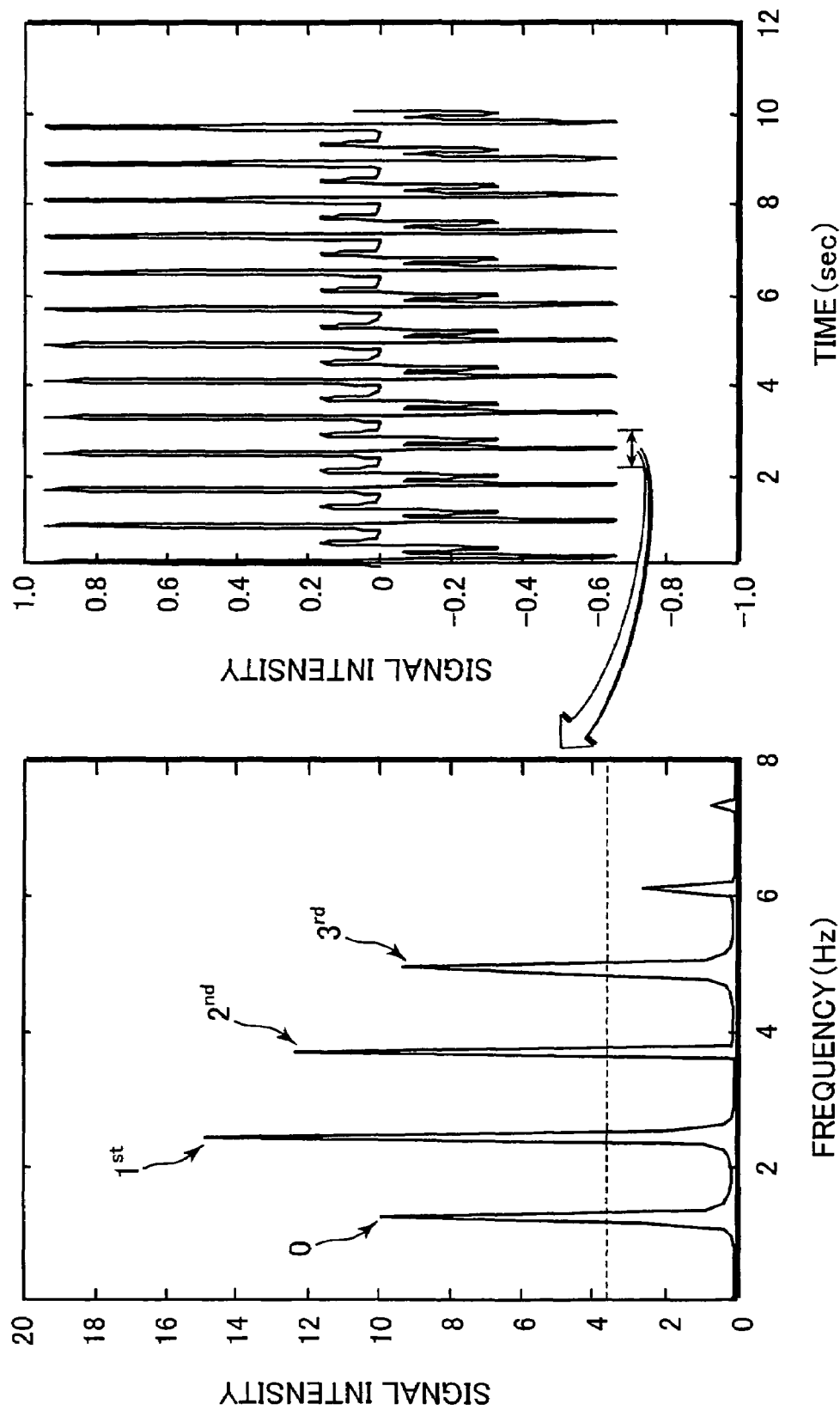
FIG. 9 is a graph showing an exemplary frequency intensity distribution of the age of forties.
Figure 10:
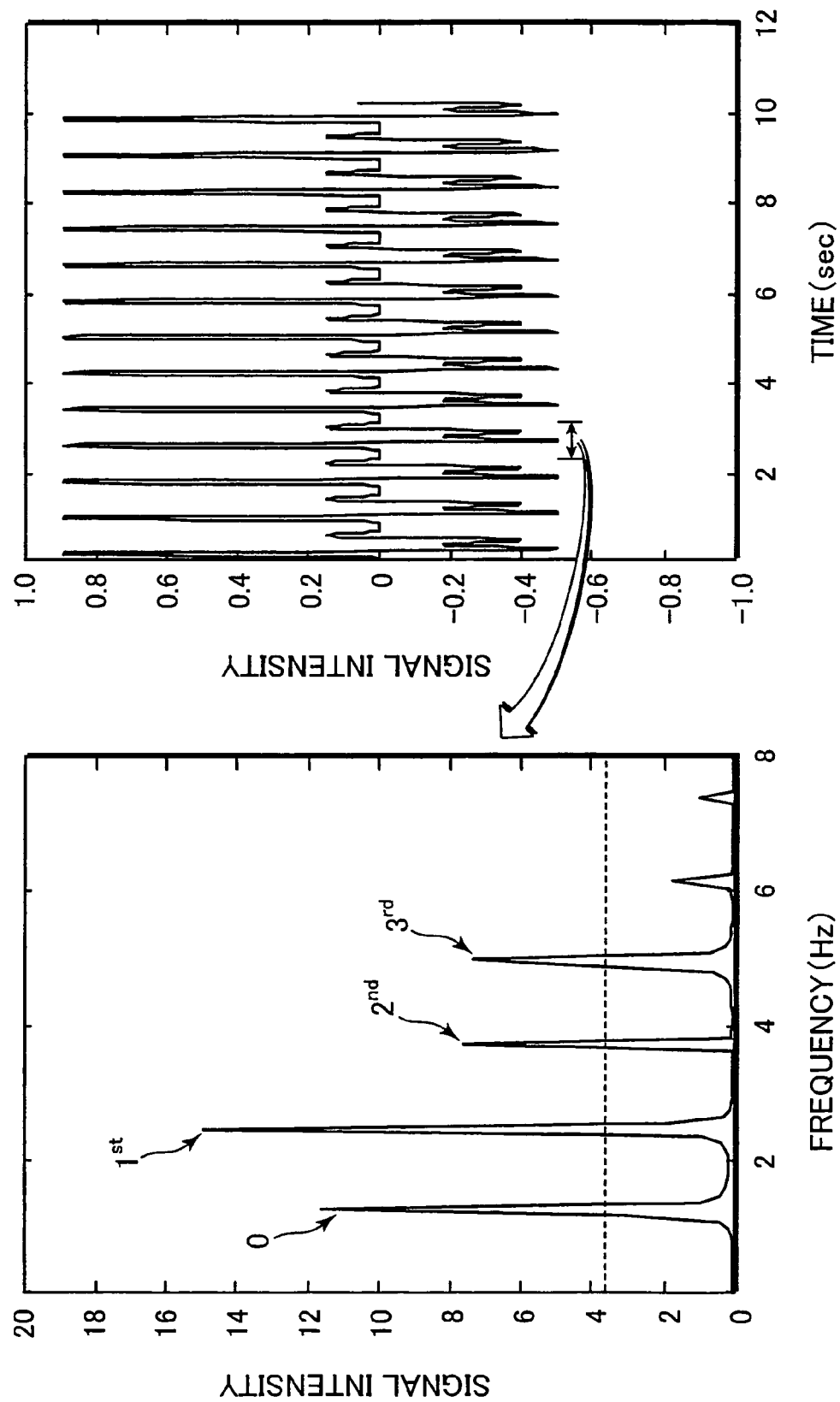
FIG. 10 is a graph showing an exemplary frequency intensity distribution of the age of fifties.

The reference frequency calculator 2931 calculates a reference frequency (f), i.e., the 0-th to third reference frequencies, from the frequency intensity distribution. With reference to FIG. 7, specifically, the reference frequency calculator 2931 calculates a frequency whose intensity exceeds a predetermined threshold 703 in a frequency band 702 in the frequency intensity distribution of a part 701 of the pulse wave, and then determines the calculated frequency as a reference frequency. The reference frequency calculator 2931 calculates, based on calculated reference frequencies, a second reference frequency (f2) having the tendency to lower according to age and a first reference frequency (f1) to be used for the normalization of the second reference frequency (f2).

The frequency intensity calculator 2932 calculates an intensity (p) of the reference frequencies calculated by the reference frequency calculator 2931. The frequency intensity calculator 2932 calculates an intensity of each reference frequency by integrating frequency intensities within a predetermined range having a center at the reference frequency. More detailed description is given referring to FIG. 8. The frequency intensity calculator 2932 calculates a reference frequency intensity by integrating intensities within predetermined ranges (e.g., a range 803) having a center at the reference frequencies (e.g., a peak frequency 802) in the frequency intensity distribution of a part 801 of the pulse wave. In this way, the frequency intensity calculator 2932 calculates a first reference frequency intensity (p1) and a second reference frequency intensity (p2) corresponding to the first reference frequency and the second reference frequency. Integration is carried out in the calculation of a frequency intensity in order to calculate a frequency intensity characteristic value not using an intensity at a point (peak frequency) of the reference frequency (i.e., not using one Sin waveform information based on Fourier transform), but using intensities in a mountain-shaped area (information abut the mountain shape) of the reference frequency (i.e., using information about the entire area of the reference frequency approximated by Sin). In other words, instead of using information about one point, such as the maximum value point, minimum value point in the above-mentioned prior art, information relating to all points (characteristic points) on the frequency space is used to calculate more accurate frequency intensity and then more accurate frequency intensity characteristic value and vessel age. The integration range of each reference frequency may be set in a range excluding the both foot portions of the waveform (mountain) of the reference frequency, or alternatively in a range including the both foot portions.

The frequency intensity characteristic value calculator 2933 calculates a frequency intensity characteristic value of each part of the pulse wave. Specifically, the frequency intensity characteristic value calculator 2933 first normalizes a certain reference frequency intensity of a pulse part of the pulse wave using another certain reference frequency intensity. In this embodiment, the second reference frequency intensity p2 whose fluctuation relates with the age is normalized by dividing it with the first reference frequency intensity p1. This normalization is shown by Equation: qi (p1, p2)=p2/p1, wherein the reference "qi (p1, p2)" denotes data calculated by normalizing as described above, and qi is a function of p1 and p2, and the mark "/" denotes division. Such calculation is carried out for N parts of the pulse wave, and an average value Q of the calculated data for N parts is calculated by Equation: Q=Σqi (p1,p2)/N. The average value Q is a frequency intensity characteristic value (Q). In this embodiment, not 0-th reference frequency intensity but the first reference frequency intensity is used for the normalization. The reason why the 0-th reference frequency intensity is not used is as follows: 1) Reference frequency intensities are calculated for a number of pulse parts of the pulse wave; 2) However, there is a likelihood that the 0-th reference frequency intensity corresponding to the beat is not suitably obtained, and is not used for normalization. However, this does not mean that the 0-th frequency intensity never be used. It may be used if necessary.

The pulse wave property analyzer 294 analyzes the frequency intensity characteristic value information calculated by the frequency intensity characteristic value calculator 2933 to thereby obtain a pulse wave property. In this embodiment, a vessel age is calculated from the frequency intensity characteristic value as a pulse wave property. Specifically, the pulse wave property analyzer 294 is provided with a conversion information memory 2941 which stores conversion information, e.g., a conversion table (LUT). A vessel age corresponding to a frequency intensity characteristic value Q is calculated by converting data using the conversion table (or equation). This conversion is generally a nonlinear conversion.

Figure 11:
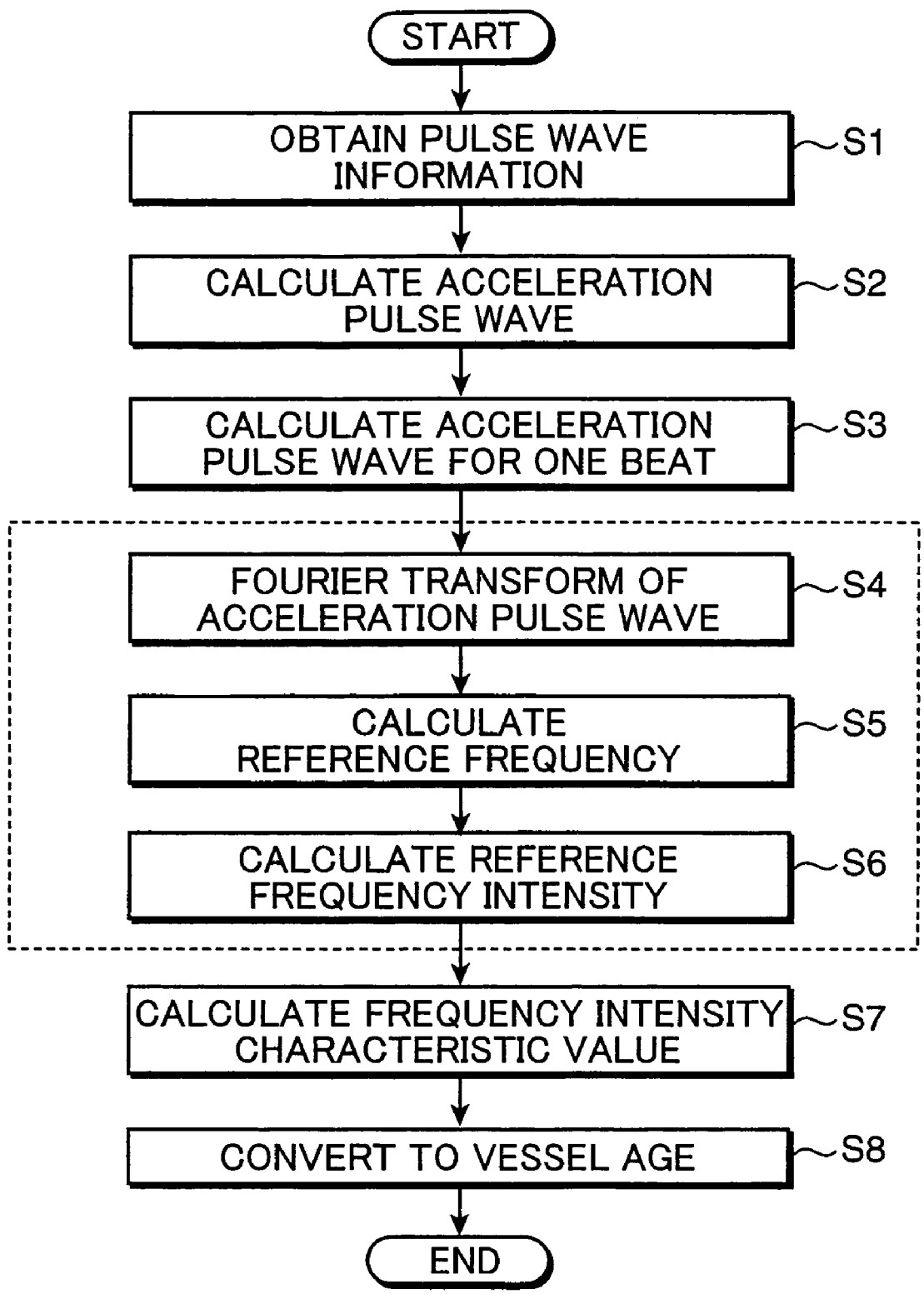
FIG. 11 is a flowchart showing a sequence of operations of estimating blood vessel age in the biological information processing apparatus.

FIG. 11 is a flowchart showing a sequence of operations of the biological information processing apparatus 1 to estimate a vessel age, according to the first embodiment of the invention. First, pulse wave information of a living body (subject) is obtained by the measuring unit 10, and is then sent to the controller 29 (Step S1). Next, the acceleration pulse wave calculator 291 calculates an acceleration pulse wave by taking the second derivative of the pulse wave (Step S2), and calculates an acceleration pulse wave for one beat from the calculated acceleration pulse wave (Step S3). Subsequently, the Fourier transformer 292 carries out a discrete Fourier transform of acceleration pulse wave signals for N successive pulse parts ($t_i$–$t_{i+1}$) of the pulse wave to thereby calculate a frequency intensity distribution for each pulse part of the pulse wave (Step S4). The reference frequency calculator 2931 calculates the 0-th to third reference frequencies (f0 to f3) from the calculated frequency intensity distribution calculated by the Fourier transformer 292 (Step S5), and the frequency intensity calculator 2932 integrates intensities within a range having a center at the reference frequency or peak position to thereby calculate a reference frequency intensity (Step S6). The frequency intensity characteristic value calculator 2933 calculates a frequency intensity characteristic value by normalizing the second reference frequency intensity p2 using the first reference frequency intensity p1, that is, p2/p1 (Step S7). The pulse wave property analyzer 294 carries out data conversion of the calculated frequency intensity characteristic value using the conversion table to thereby calculate or estimate a vessel age (Step S8).

The frequency analysis (calculation of reference frequency intensity) described above is an analysis carried out assuming that the pulse wave is a periodic function having a waveform continuing infinitely. However, an actual pulse wave is localized. Accordingly, it will be preferable to work out a suitable technique for such actual pulse wave to improve the measurement performance. First, the concept relating to this technique is theoretically described.

Figure 13:
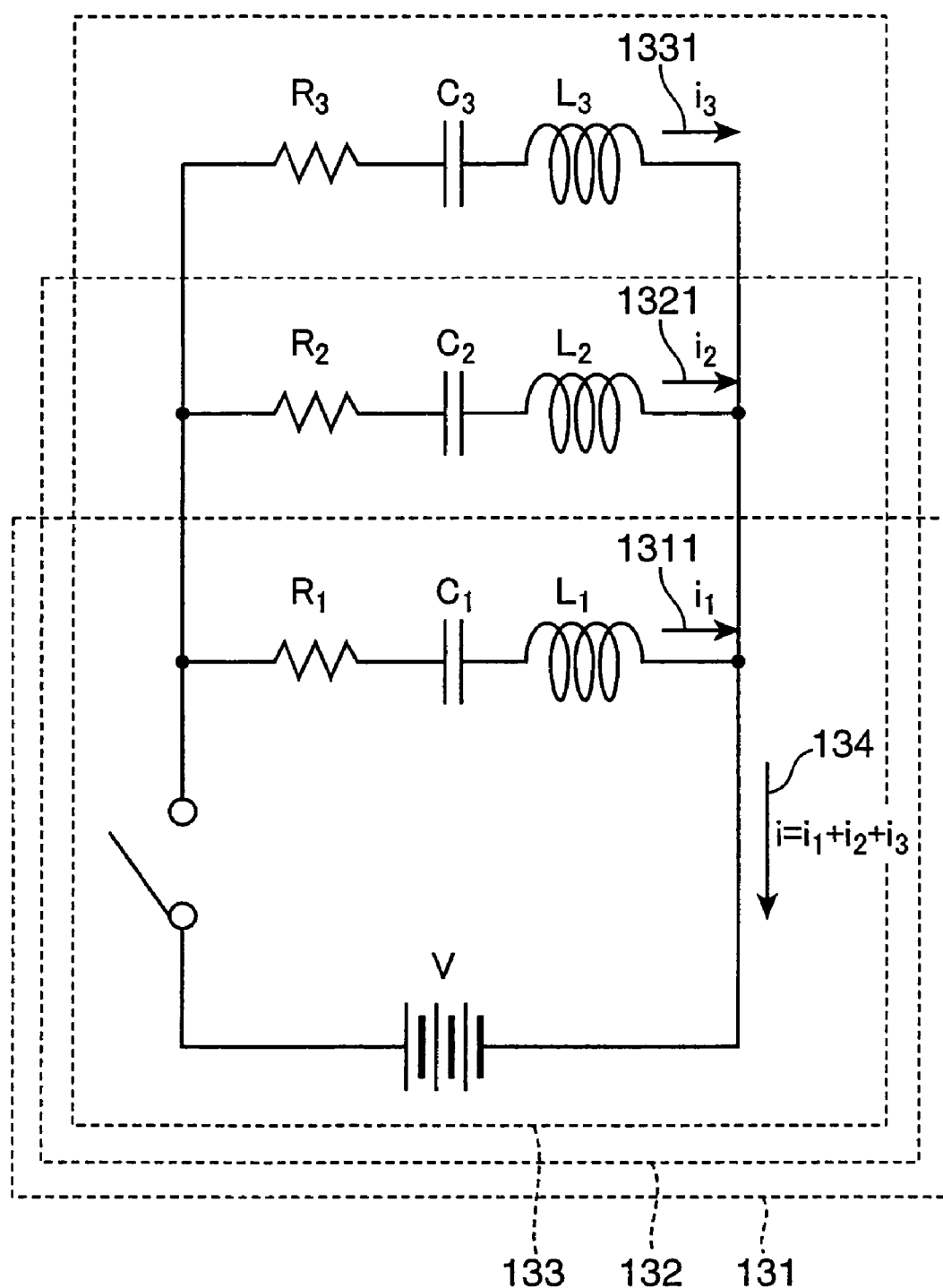
FIG. 13 is a circuit diagram showing an electrical circuit as a transient phenomenon model taking into account attenuation.

The pulse wave can be modeled as a signal which the blood vessel system outputs in response to an impulse signal corresponding to heart beats. Specifically, the pulse wave can be considered to be substantially equivalent to an electrical circuit model (LCR circuit) shown in FIG. 13 which is a transient phenomenon model taking into account the attenuation (envelope curve) characteristic. When $R1<2\sqrt{(L1/C1)}$, an output current $i_1$ shown by the arrow indicated at 1311 in a first partial circuit (part LCR circuit) inside the dotted frame indicated at 131 in FIG. 13 is expressed by the following Equation (2):

$$i_1 = p_1 e^{(-\tau_1^{-1} + j\omega_1)t} \qquad (2)$$

Figure 14:
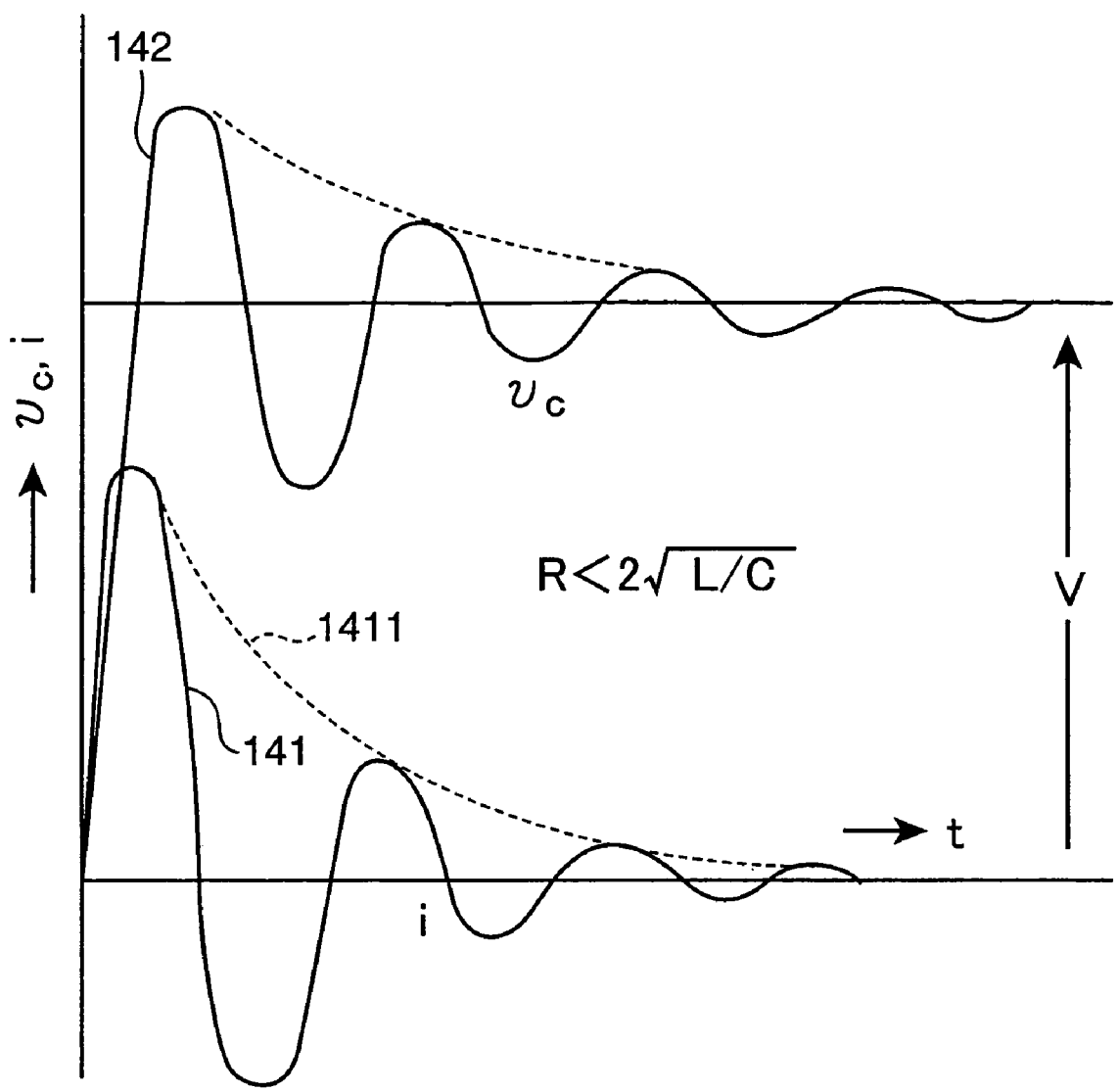
FIG. 14 is a graph showing attenuation curves of output current and output voltage in the electrical circuit shown in FIG. 13.

Equation (2) can be shown as an attenuation curve 141 (attenuation curve of the output current i) shown in FIG. 14. Also, FIG. 14 shows an attenuation curve 142 of an output current Vc which has a phase difference from the attenuation curve 141. The term τ1 in Equation (2) denotes time constant of an envelope curve 1411 on the attenuation curve 141 of the output current I, and the term ω1(=2pf1) denotes an angular frequency. The term f1 of the angular frequency corresponds to the first reference frequency described with reference to the first embodiment.

For the second reference frequency and the third reference frequency, similarly, an output current $i_2$ shown by the arrow indicated at 1321 in the second partial circuit inside the dotted frame indicated at 132 and an output current $i_3$ shown by the arrow indicated at 1331 in the third partial circuit inside the dotted frame indicated at 133 are obtained, and the output currents $i_1$ to $i_3$ of the first to third partial circuits are summed up (superimposed) to output an output current i shown by the arrow indicated at 134.

In the calculation of the first to third reference frequencies, it will be seen that there are a total of nine unknown quantities because Equation (2) corresponding to each reference frequency has three unknown quantities p, t and ω. If nine time values are given for an acceleration pulse wave for one beat, accordingly, each reference frequency can be obtained by solving the following simultaneous Equation (3):

$$\begin{cases} i(t_1) = p_1 e^{(-\tau_1^{-1}+j\omega_1)t_1} + p_2 e^{(-\tau_2^{-1}+j\omega_2)t_1} + p_3 e^{(-\tau_3^{-1}+j\omega_3)t_1} \\ i(t_2) = p_1 e^{(-\tau_1^{-1}+j\omega_1)t_2} + p_2 e^{(-\tau_2^{-1}+j\omega_2)t_2} + p_3 e^{(-\tau_3^{-1}+j\omega_3)t_2} \\ \vdots \\ i(t_9) = p_1 e^{(-\tau_1^{-1}+j\omega_1)t_9} + p_2 e^{(-\tau_2^{-1}+j\omega_2)t_9} + p_3 e^{(-\tau_3^{-1}+j\omega_3)t_9} \end{cases} \qquad (3)$$

After obtaining p1, p2 and p3 which are the first, second and third reference frequency intensities by solving the above simultaneous equation, similarly to the foregoing embodiment, a frequency intensity characteristic value (Q) can be obtained by dividing p2 by p1 (p2/p1), and a vessel age can be estimated from the calculated frequency intensity characteristic value.

In Equation (3), however, the parameters t and co are nonlinear, which make calculation troublesome. For this reason, Equation (3) is applied with a general linearizing technique in which standard values of the parameters τ and ω are calculated from an average pulse wave pattern, and Equation (3) is Taylor expanded about the calculated standard values, and approximated by 0-th and first factors, and the following Equation (4) is thus obtained:

$$\begin{bmatrix} i(t_1) \\ i(t_2) \\ \vdots \\ i(t_9) \end{bmatrix} = \begin{bmatrix} a_1^1 - b_1^1\bar{\tau}_1 - c_1^1\bar{\omega}_1 & a_2^1 - b_2^1\bar{\tau}_2 - c_2^1\bar{\omega}_2 & a_3^1 - b_3^1\bar{\tau}_3 - c_3^1\bar{\omega}_3 & b_1^1 & c_1^1 & b_2^1 & c_2^1 & b_3^1 & c_3^1 \\ a_1^2 - b_1^2\bar{\tau}_1 - c_1^2\bar{\omega}_1 & a_2^2 - b_2^2\bar{\tau}_2 - c_2^2\bar{\omega}_2 & a_3^2 - b_3^2\bar{\tau}_3 - c_3^2\bar{\omega}_3 & b_1^2 & c_1^2 & b_2^2 & c_2^2 & b_3^2 & c_3^2 \\ & & \vdots & & & & & & \\ a_1^9 - b_1^9\bar{\tau}_1 - c_1^9\bar{\omega}_1 & a_2^9 - b_2^9\bar{\tau}_2 - c_2^9\bar{\omega}_2 & a_3 - b_3^9\bar{\tau}_3 - c_3^9\bar{\omega}_3 & b_1^9 & c_1^9 & b_2^9 & c_2^9 & b_3^9 & c_3^9 \end{bmatrix} \begin{bmatrix} p_1 \\ p_2 \\ p_3 \\ \tau_1 p_1 \\ \omega_1 p_1 \\ \tau_2 p_2 \\ \omega_2 p_2 \\ \tau_3 p_3 \\ \omega_3 p_3 \end{bmatrix} \quad (4)$$

$$a_r^k = e^{(-\tau_r^{-1} + j\bar{\omega}_r)t_k}$$

$$b_r^k = e^{(-\tau_r^{-2} + j\bar{\omega}_r)t_k}$$

$$c_r^k = je^{(-\tau_r^{-1} + j1)t_k}$$

$\bar{\tau}_r$: standard value of $\tau_r$ $\bar{\omega}_r$: standard value of $\omega_r$ Thus, values p1, p2 and p3 are calculated by solving Equation (4).

The flow of this processing is identical to that shown in FIG. 11 except for that the operations of Steps S4 to S6 within the dotted frame are replaced with the steps for solving the simultaneous equations. The signals in the first embodiment are defined in the Fourier base. In this processing, however, the signal is defined in the base taking into account frequency attenuation, which is substantially equivalent to that of the first embodiment in the processing. Accordingly, any modifications of the first embodiment may be easily applicable for the information processing considering the frequency attenuation.

Figure 12:
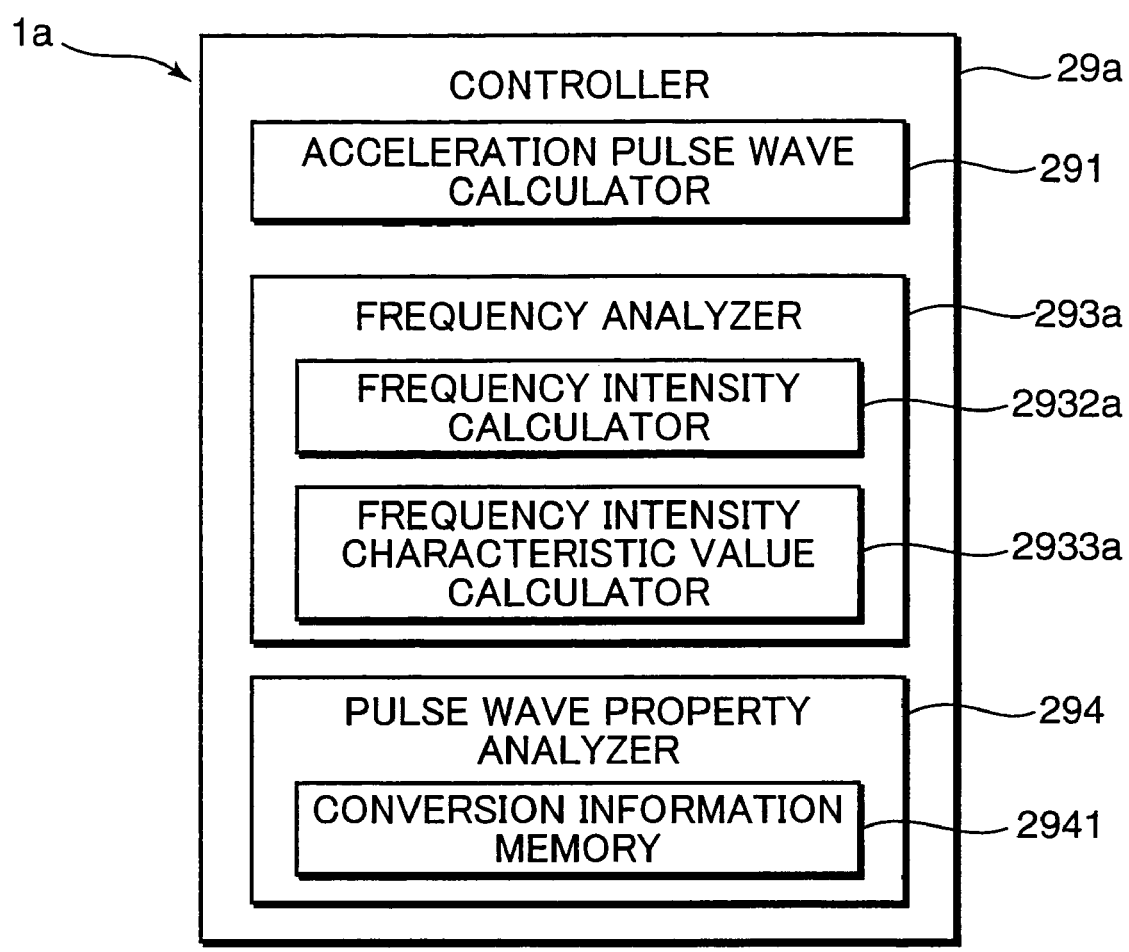
FIG. 12 is a block diagram showing functions of a controller provided in a biological information processing apparatus according to a second embodiment of the invention.

FIG. 12 is a block diagram showing each function of a controller 29a of a biological information processing apparatus 1a according to a second embodiment, which considers the frequency attenuation. The controller 29a of the biological information processing apparatus 1a differs from the controller 29 of the biological information processing apparatus 1 in that the controller 29a does not include the Fourier transformer 292, and the frequency analyzer 293a differs from the frequency analyzer 293. The other operation sections being given with like numerals are the same as those of the biological information processing apparatus 1, and further description about them is omitted. The frequency analyzer 293a includes a frequency intensity calculator 2932a and a frequency intensity characteristic value calculator 2933a. The frequency intensity calculator 2932a calculates first to third reference frequency intensities p1 to p3 in accordance with Equation (4) (or Equation (3)).

The frequency intensity calculator 2932a extracts nine measurement values from the acceleration pulse wave calculated by the acceleration pulse wave calculator 291. The nine measurement values are minimum required to solve the simultaneous equation, and correspond to predetermined time (measurement points) on the calculated acceleration pulse wave. Putting the nine measurement values in the corresponding terms of to equation (4) as initial parameters, Equation (4) is solved to obtain the first to third reference frequency intensities p1 to p3. Upon calculating each frequency intensity, unknown angular frequencies ω, which are reference frequencies (f1 to f3), are also calculated. The frequency intensity characteristic value calculator 2933a uses the reference frequency intensities calculated by the frequency intensity calculator 2932a, in this embodiment the first and second reference frequency intensities p1 and p2, to determine a frequency intensity characteristic value (Q) by diving p2 by p1 (p2/p1).

In this way, the frequency analyzer 293a carries out the calculation according to the above-described electric circuit model modeling the pulse wave to thereby calculate the frequency intensities from the pulse wave information (the acceleration pulse wave calculated by the acceleration pulse wave calculator 291) obtained from the measuring unit 10, and determine the frequency intensity characteristic value from the frequency intensities. The pulse wave property analyzer 294 calculates a vessel age from the frequency intensity characteristic value.

Figure 15:
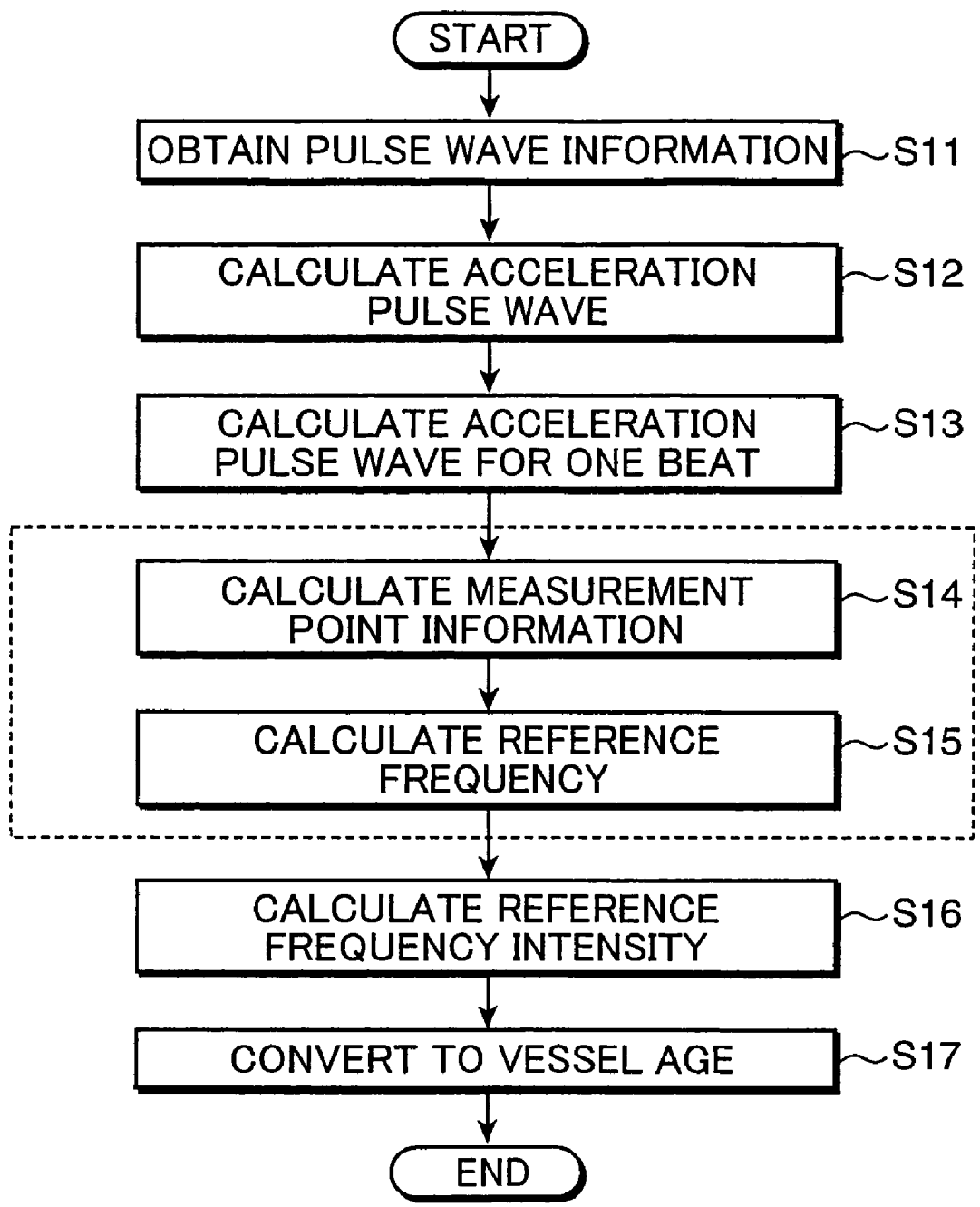
FIG. 15 is a flowchart showing a sequence of operations of estimating blood vessel age in the biological information processing apparatus according to the second embodiment of the invention.

FIG. 15 is a flowchart showing a sequence of operations of estimating a vessel age by the biological information processing apparatus 1a according to the second embodiment. First, pulse wave information of the living body (subject) is obtained by the measuring unit 10, and is then sent to the controller 29 (Step S11). The acceleration pulse wave calculator 291 takes the second derivative of the pulse wave to obtain the acceleration pulse wave (Step S12), and obtain then the acceleration pulse wave for one beat from the calculated acceleration pulse wave (Step S13). Next, the frequency intensity calculator 2932a extracts the information at the predetermined number of measurement points (i.e., nine measurement values) from the acceleration pulse wave for one beat calculated in Step S13 (Step S14), and the reference frequency intensities i.e., the first to third reference frequency intensities p1 to p3) are calculated by solving the simultaneous equation according to the electric circuit model modeling a pulse wave having the measurement point information as the initial parameters (Step S15). The frequency intensity characteristic value calculator 2933a uses the reference frequency intensities calculated in Step S15, i.e., the first reference frequency intensity P1 and the second reference frequency intensity p2, to calculate the frequency intensity characteristic value by dividing the second reference frequency intensity p2 with the first reference frequency intensity p1 (p2/p1) (Step S16). Finally, the vessel age is calculated or estimated by converting the calculated characteristic value using the conversion table. (Step S17)

In the biological information processing apparatus 1 (1a) according to the first (second) embodiment, the measuring unit 10 (pulse wave acquirer) acquires pulse wave information of the living body, and the frequency analyzer 293 (293a) analyzes the frequency of the pulse wave according to the pulse wave information acquired from the measurement unit 10. Further, the frequency intensity characteristic value calculator 2933 (2933a) (characteristic value extractor) extracts the predetermined characteristic value (reference frequency intensity characteristic value) from the pulse wave frequency information (reference frequency and reference frequency intensity) obtained by analysis using the frequency analyzer 293 (293a), and the pulse wave property analyzer 294 (pulse wave property calculator) calculates the pulse wave property (vessel age) according to the frequency intensity characteristic value extracted by the frequency intensity characteristic value calculator 2933 (2933a). Accordingly, this analysis can be seen to be different from the conventional analysis carried out based on information at points, such as maximum value point, minimum value point. In the first and second embodiments, the analysis is carried out based on-wide range data (but not required to use all frequency information) or based on the solution of the equation according to the transient phenomenon model or the electric circuit model defined in the second embodiment. The characteristic value (frequency intensity characteristic value Q) is calculated based on the pulse wave frequency information (reference frequency intensity) obtained by the analysis, and the pulse wave property (vessel age) is calculated according to the characteristic value. Thus, it is possible to provide a biological information processing apparatus whose operation is not influenced by noise components at the time of acquiring pulse wave information (the operation is robust against noises), and which can suppress any error in the evaluation (pulse wave property) due to pulse wave fluctuation, and which is strong against disturbances to ensure stable operation and provide an evaluation value with high accuracy.

The pulse wave property analyzer 294 calculates the vessel age as the pulse wave property by carrying out the data conversion to the characteristic value using predetermined conversion data. Accordingly, the arithmetic operation of estimating the vessel age can be easily performed by using the conventional method of data conversion.

The frequency analyzer 293 (293a) analyzes the acceleration pulse wave which is obtained by taking the second derivative of the pulse wave. Accordingly, steady components, which cannot be used for the frequency analysis, can be easily removed to thereby enable more accurate frequency analysis.

The frequency analyzer 293 (293a) extracts the partial pulse wave information for one beat from the pulse wave information, and analyzes the extracted partial pulse wave information. This will avoid the problem that a large error is caused in the evaluation due to information on pulse wave for a number of beats having variations in time. Accordingly, the frequency analysis can be steadily performed at decreased measurement error or suppressed variation in the measurement data.

The frequency analyzer 293 calculates the characteristic value based on at least two extreme values (i.e., the first and second reference frequency intensities p1, p2) in the frequency intensity distribution calculated as the pulse wave frequency information. Accordingly, the calculation absorbs pulse wave variations in time and differences among the subjects to provide accurate values.

The frequency analyzer 293 calculates the characteristic value based on the frequency intensity information obtained by integrating frequency intensities of a predetermined frequency range having a center at the extreme value (peak value) in the frequency intensity distribution. The calculation does not use the frequency intensity at the particular point, i.e., maximum value point or minimum value point, but uses the frequency intensities at all the points in the predetermined range on the frequency intensity distribution. Accordingly, the value estimation is prevented from being influenced by a small variation in the pulse wave, thereby providing characteristic values not having large differences between them. In other words, more accurate characteristic value can be calculated to ensure more accurate pulse wave property or vessel age.

The frequency analyzer 293 carries out analysis (frequency analysis or vessel age estimation based on the frequency analysis) based on the data obtained in the Fourier transform by the Fourier transformer 293. In other words, the analysis can be accomplished more efficiently using the Fourier transform which is widely used and simple.

The frequency analyzer 293a carries out analysis according to the transient phenomenon model, and can thus reduce the influence of noises (disturbance) at the time of analysis and ensure more accurate analysis taking into account the transient phenomenon, that is, the attenuation characteristic (envelope curve).

The frequency analyzer 293a carries out analysis according to the electric circuit model as the transient phenomenon model whereby the pulse wave is assumed to be an output signal in response to a predetermined impulse signal. In other words, the analysis (arithmetic operation) can be executed by the simple method using the electric circuit mode.

The frequency analyzer 293a carries out the analysis according to the electric circuit model by solving the simultaneous equation (Equation (4) or (3)) having unknown frequency intensities for the calculation of characteristic value by using actual measurement values corresponding to the predetermined number of times in the partial pulse wave information for one beat. In other words, the simultaneous equation is solved by using the actual measurement values (values at the predetermined times) in the partial pulse wave information (pulse wave duration $t_i$-$t_{i+1}$) as the initial parameters. Accordingly, the frequency intensities for the calculation of characteristic value can be obtained assuredly by the simple method.

The operation program for use in the biological information processing apparatus 1 (1a) according to the first (second) embodiment allows the measuring unit 10 (pulse wave acquirer) to acquire pulse wave information of the living body, and allows the controller 29 (29a) or computer to execute a step of causing the frequency analyzer 293 (293a) to analyze the pulse wave frequency based on the pulse wave information acquired from the measuring unit 10, a step of causing the frequency intensity characteristic value calculator 2933 (2933a) (characteristic value extractor) to calculate a characteristic value (reference frequency intensity characteristic value) based on the pulse wave frequency information (reference frequency and reference frequency intensities) obtained by the analysis carried out by the frequency analyzer 293 (293a), and a step of causing the pulse wave property analyzer 294 (pulse wave property calculator) to calculate a pulse wave property (vessel age) based on the characteristic value calculated by the frequency intensity characteristic value calculator 2933 (2933a).

Accordingly, this analysis can be seen to be different from the conventional analysis carried out based on information at points, such as maximum value point, minimum value point. In the first and second embodiments, the analysis is carried out based on wide range data. The characteristic value is calculated based on the pulse wave frequency information obtained by the analysis, and the pulse wave property is calculated based on the characteristic value. Thus, it is possible to provide an operation program for use in a biological information processing apparatus and a biological information apparatus operated with the program whose operation is not influenced by noise components at the time of acquiring pulse wave information (the operation is robust against noises), and which can suppress any error in the evaluation (pulse wave property) due to pulse wave fluctuation, and which is strong against disturbances to ensure stable operation and provide an evaluation value with high accuracy.

Further, the invention may be modified as follows.

(A) In the first embodiment, the second reference frequency component (second reference frequency intensity p2) in the frequency intensity distribution is normalized by using the first reference frequency component (first reference frequency intensity p1), i.e., (p2/p1). However, the normalization of reference frequency component is not limited to this manner, and the third reference frequency component (third reference frequency intensity) and other subsequent reference frequency components may be used for the normalization. For instance, the second reference frequency intensity p2 may be normalized by using the third reference frequency intensity p3, i.e., (p2/p3) or by using the fourth reference frequency intensity p4, i.e., (p2/p4). Also, it may be needless to say that the 0-th reference frequency intensity can be used. In the foregoing embodiments, the characteristic value is calculated by normalizing the second reference frequency intensity which is clearly related with the age. However, other reference frequency intensity, e.g., the third reference frequency intensity, may be normalized to obtain a characteristic value by using the first reference frequency intensity or other reference frequency intensity as described above.

(B) In the first embodiment, a characteristic value is calculated by normalizing the single reference frequency intensity, i.e., the second reference frequency intensity. However, it may be appreciated to calculate a characteristic value by combining a predetermined number of reference frequency intensities from the 0-th to fourth (or more) reference frequency intensities, for example, q'(p1, p2, p3)=(w2×p2+w3×p3)/p1 wherein q' (p1, p2, p3) denotes a function of p1, p2 and p3, w denotes a predetermined constant, and the mark "×" denotes multiplication. For the normalization, a given reference frequency intensity can be used. Also, it may be appreciated to generalize and define a function q" (p1, p2, p3). The third reference frequency component has information relating to the vessel age. For the age having smaller variations in the second reference frequency component, accordingly, it may be appreciated to define a function which has a noticeable relationship of the third reference frequency component with the characteristic value.

(C) In the first and second embodiments, the frequency intensity characteristic value may be calculated not by normalizing the reference frequency intensity but by directly using the reference frequency intensity.

(D) In the first and second embodiments, the pulse wave itself (raw measurement data not subjected to any processing such as taking derivative) may be used for the analysis instead of the acceleration pulse wave.

(E) In the first and second embodiments, the pulse wave property (vessel age) is calculated or estimated from the frequency intensity characteristic value. However, it may be appreciated to calculate a pulse wave property directly from pulse wave data (acceleration pulse wave data) or frequency intensity distribution data by a conversion table which is prepared in advance.

(F) In the first embodiment, the Fourier transform is carried out for repeated waveform patterns or continuous pulse wave durations, respectively. However it may be appreciated to carry out window Fourier transform of a single waveform pattern using a window function, such as a rectangular window function, a Gaussian window function. In this case, the 0-th reference frequency component becomes zero. Also, the frequency analysis may be carried out using the Laplace transform, the Z-transform, or the wavelet instead of the Fourier transform. In the case of using wavelet, analysis can be accomplished even if the data does not have a periodic function.

(G) In the second embodiment, nine measurement values are extracted or used from the pulse wave signal to solve the simultaneous equation. However, it may be appreciated to use ten or more measurement values which are larger than the nine measurement values necessary to solve the equation. In this case, the least squares method is done for those exceeding the necessary nine measurement values. The use of more measurement values will make the influence of noises to the analysis less, or stronger against noises. Also, it may be appreciated to use all the measurement values at all the points of the pulse wave signal.

(H) In the second embodiment, the simultaneous equation consisting of nine equations with respect to the first to third reference frequency intensities (p1 to p3) is provided. However, the number of equations is not limited to nine. For example, it may be appreciated to use a simultaneous equation consisting of 3n equations with respect to the first reference frequency intensity (p1) to the n-th reference frequency intensity (pn), wherein n denotes the number is equal to or larger than 2. The number of measurement values to be extracted follows the way described in (G).

(I) In the second embodiment, the time constants $t_1$, $t_2$ and $t_3$ may be used for calculation of a characteristic value, thereby improving the accuracy of the calculation.

(J) In the second embodiment, predetermined standard values may be used in a part of the arithmetic parameters of the transient phenomenon model. For instance, a reference frequency obtained by the Fourier transform in the first embodiment may be used as the standard value of the angular frequency ω. In this case, a Fourier transformer 292 is provided in the controller 29a shown in FIG. 12. This will simplify the calculation. The standard value of the time constant t may be separately calculated based on an envelope curve on the first reference frequency (first peak value) and the second reference frequency (second peak value) of the pulse wave waveform. In this case, it is sufficient to extract three measurement values from the pulse wave information. The equation is further simplified as Equation (5) shown below. It should be noted that for the calculation of the standard value, the measurement value at the peak point is not necessarily required, but measurement values at desired points on the envelope curve may be used.

$$\begin{bmatrix} i(t_1) \\ i(t_2) \\ i(t_3) \end{bmatrix} = \begin{bmatrix} a_1^1 & a_2^1 & a_3^1 \\ a_1^2 & a_2^2 & a_3^2 \\ a_1^3 & a_2^3 & a_3^3 \end{bmatrix} \begin{bmatrix} p_1 \\ p_2 \\ p_3 \end{bmatrix} \quad (5)$$

As described above, a biological information processing apparatus comprises a pulse wave acquirer for acquiring information about a pulse wave of a living body, a frequency analyzer for analyzing the frequency of the pulse wave based on the pulse wave information acquired by the pulse wave acquirer, a characteristic value extractor for extracting a characteristic value from the pulse wave frequency information obtained by the frequency analyzer, and a pulse wave property calculator for calculating a pulse wave property based on the characteristic value extracted by the characteristic value extractor.

With this configuration, the biological pulse wave information is obtained by the pulse wave acquirer, and the frequency analyzer carries out an analysis of the frequency of the pulse wave based on this information. The characteristic value extractor extracts the characteristic value from the pulse wave frequency information obtained by analysis carried out by the frequency analyzer, and the pulse wave property calculator calculates the pulse wave property based on the characteristic value extracted by the characteristic value extractor.

This frequency analysis is not based on frequency information at a point, such as a maximum value point or a minimum value point, but based on frequency information over a wide range. The characteristic value is calculated based on the pulse wave frequency information obtained by the analysis, and the pulse wave property is calculated based on the characteristic value. Accordingly, the biological information processing apparatus is not influenced by noises, and is free from any large error in the evaluation value (pulse wave property) likely to be caused by slight pulse wave fluctuation, and is stable and strong against the disturbances. Thus, the evaluation value can be obtained with higher accuracy.

The pulse wave property calculator may preferably carry out data conversion using predetermined conversion information with respect to characteristic value to thereby calculate a pulse wave property indicative of the age of the blood vessel. With this configuration, the pulse wave property calculator calculates the pulse wave property or the blood vessel age by converting the characteristic value data according to the predetermined conversion information. Accordingly, the blood vessel age can be calculated or estimated more easily by the conventionally used data conversion.

The frequency analyzer may preferably analyze an acceleration pulse wave having the second derivative of the pulse wave. With this configuration, the second derivative of the pulse wave makes it possible to easily remove steady components which cannot be used for the frequency analysis, thereby ensuring more accurate frequency analysis.

The frequency analyzer may preferably extracts information about a partial pulse wave for one beat from the pulse wave information, and analyzes the extracted partial pulse wave information. With this configuration, the information about a partial pulse wave for one beat is extracted from the pulse wave information, and is analyzed. Accordingly, this analysis can avoid the problem that a large error is caused in the evaluation due to information on pulse wave for a number of beats having variations in time. Accordingly, the frequency analysis can be steadily performed at decreased measurement error or suppressed variation in the measurement data.

The frequency analyzer may preferably calculate a frequency intensity distribution as pulse wave frequency information, and calculates the characteristic value based on at least two extreme values in the frequency intensity distribution. With this configuration, the characteristic value is calculated based on the at least two extreme values in the frequency intensity distribution. Accordingly, this calculation can absorb pulse wave variations in time and differences among the subjects.

The frequency analyzer may preferably calculate the characteristic value based on frequency intensity information obtained by integrating frequency intensities within a predetermined frequency range having a center at the extreme value in the frequency intensity distribution. With this configuration, the characteristic value is calculated based on the frequency intensity information obtained by integrating frequency intensities within the predetermined frequency range having a center at the extreme value. Accordingly, this calculation does not use the frequency information at the particular point, i.e., maximum value point or minimum value point, but uses the frequency information at all the points in the predetermined range in the frequency intensity distribution to thereby prevent the value estimation from being influenced by a small variation in the pulse wave, and provide stabilized characteristic values. In other words, more accurate characteristic value can be calculated to ensure more accurate pulse wave property or vessel age.

The frequency analyzer may preferably carry out analysis based on Fourier transform. With this configuration, an efficient analysis can be accomplished using the generally used simple method or the Fourier transform.

The frequency analyzer may preferably carry out analysis based on a transient phenomenon model. With this configuration, the influence of noises or external disturbances at the time of analysis can be suppressed to thereby ensure more accurate analysis which takes into account the transient phenomenon, that is, the attenuation characteristic (envelope curve).

The frequency analyzer may preferably carry out an analysis based on a predetermined electric circuit model as the transient phenomenon model where the pulse wave is assumed to be an output signal in response to an impulse signal. With this configuration, the analysis can be carried out in the simple way using the electric circuit model.

The frequency analyzer may preferably use actual measurement values at given times in the partial pulse wave information in the electric circuit model to solve a simultaneous equation including unknown frequency intensities to obtain an characteristic value. With this configuration, the simultaneous equation including unknown frequency intensities is solved by using the actual measurement values at the given times as the initial parameters. This will provide frequency intensities for characteristic value calculation in the simpler way.

An operation program is usable in the biological information processing apparatus including the pulse wave acquirer for acquiring pulse wave information of a living body. The operation program causes a computer to execute a step of analyzing a pulse wave frequency based on the pulse wave information obtained by the pulse wave acquirer, a step of extracting a characteristic value from the obtained pulse wave frequency information, and a step of calculating a pulse wave property based on the extracted characteristic value.

With this configuration, the analysis of the pulse wave frequency is carried out based on not information at points, i.e., maximum point value or minimum point value, but information about a wide frequency range of data. The characteristic value is calculated based on the pulse wave frequency information, and the pulse wave property is calculated based on the characteristic value. Accordingly, this operation program can make the biological information processing apparatus to be stronger against the disturbances, and operable to suppress any error in the evaluation (pulse wave property) due to pulse wave fluctuation, and to ensure stable operation and provide an evaluation value with high accuracy.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. A biological information processing apparatus comprising:
   a pulse wave acquirer which acquires information about a pulse wave of a living body;
   a frequency analyzer which analyzes a frequency of the pulse wave based on the pulse wave information acquired by the pulse wave acquirer;
   a characteristic value extractor which extracts a characteristic value from the pulse wave frequency information obtained by the frequency analyzer; and
   a pulse wave property calculator which calculates a pulse wave property indicative of a functional state of blood vessels based on the characteristic value extracted by the characteristic value extractor;
   wherein the pulse wave property calculator carries out data conversion using predetermined conversion information with respect to the characteristic value to thereby calculate the pulse wave property indicative of an age of the blood vessels.

2. The biological information processing apparatus according to claim 1, wherein the frequency analyzer analyzes an acceleration pulse wave having the second derivative of the pulse wave.

3. The biological information processing apparatus according to claim 2, wherein the frequency analyzer extracts partial pulse wave information consisting of information for one beat from the pulse wave information, and analyzes the extracted partial pulse wave information.

4. The biological information processing apparatus according to claim 3, wherein the frequency analyzer obtains a frequency intensity distribution as the pulse wave frequency information, and calculates the characteristic value based on at least two extreme values in the frequency intensity distribution.

5. The biological information processing apparatus according to claim 4, wherein the frequency analyzer calculates the characteristic value based on frequency intensity information obtained by integrating frequency intensities within a predetermined frequency range having a center at the extreme value in the frequency intensity distribution.

6. The biological information processing apparatus according to claim 5, wherein the frequency analyzer carries out analysis based on Fourier transform.

7. The biological information processing apparatus according to claim 1, wherein the frequency analyzer extracts partial pulse wave information consisting of information for one beat from the pulse wave information, and analyzes the extracted partial pulse wave information.

8. The biological information processing apparatus according to claim 1, wherein the frequency analyzer obtains a frequency intensity distribution as the pulse wave frequency information, and calculates the characteristic value based on at least two extreme values in the frequency intensity distribution.

9. The biological information processing apparatus according to claim 1, wherein the frequency analyzer carries out analysis based on Fourier transform.

10. The biological information processing apparatus according to claim 1, wherein the frequency analyzer carries out analysis based on a transient phenomenon model.

11. A biological information processing apparatus comprising:
    a pulse wave acquirer which acquires information about a pulse wave of a living body;
    a frequency analyzer which analyzes a frequency of the pulse wave based on the pulse wave information acquired by the pulse wave acquirer;
    a characteristic value extractor which extracts a characteristic value from the pulse wave frequency information obtained by the frequency analyzer; and
    a pulse wave property calculator which calculates a pulse wave property based on the characteristic value extracted by the characteristic value extractor;
    wherein the frequency analyzer carries out analysis based on a transient phenomenon model.

12. The biological information processing apparatus according to claim 1, wherein the frequency analyzer carries out an analysis based on an electric circuit model as the transient phenomenon model where the pulse wave is assumed to be an output signal in response to an impulse signal.

13. The biological information processing apparatus according to claim 12, wherein the frequency analyzer uses actual measurement values at given times in partial pulse wave information to solve a simultaneous equation including unknown frequency intensities in the electric circuit model, thereby calculating the characteristic value.

14. A biological information processing apparatus comprising:
    a pulse wave acquirer which acquires information about a pulse wave of a living body;
    a frequency analyzer which analyzes a frequency of the pulse wave based on the pulse wave information acquired by the pulse wave acquirer;
    a characteristic value extractor which extracts a characteristic value from the pulse wave frequency information obtained by the frequency analyzer; and
    a pulse wave property calculator which calculates a pulse wave property indicative of an age of blood vessels based on the characteristic value extracted by the characteristic value extractor;
    wherein the frequency analyzer obtains a frequency intensity distribution as the pulse wave frequency information, and calculates the characteristic value based on at least two extreme values in the frequency intensity distribution.

15. A computer readable medium containing a computer executable program for use in a biological information processing apparatus including a pulse wave acquirer for acquiring pulse wave information of a living body, the program comprising computer executable code to cause a computer to execute:
    a step of analyzing a pulse wave frequency based on the pulse wave information acquired by the pulse wave acquirer, a step of extracting a characteristic value from the obtained pulse wave frequency information, and
    a step of calculating a pulse wave property indicative of a functional state of blood vessels based on the extracted characteristic value,
    wherein the step of calculating the pulse wave property includes data conversion using predetermined conversion information with respect to the characteristic value to thereby calculate the pulse wave property indicative of an age of the blood vessels.

16. A biological information processing apparatus comprising:
    a pulse wave acquirer which is configured to acquire information about a pulse wave of a living body;

a frequency analyzer which is configured to analyze a frequency of the pulse wave based on the pulse wave information acquired by the pulse wave acquirer;

a characteristic value extractor which is configured to extract a characteristic value from the pulse wave frequency information obtained by the frequency analyzer; and a pulse wave property calculator which is configured to calculate a pulse wave property indicative of an age of blood vessels in the living body based on the characteristic value extracted by the characteristic value extractor.

* * * * *

UNITED STATES PATENT AND TRADEMARK OFFICE
CERTIFICATE OF CORRECTION

PATENT NO. : 7,566,306 B2  Page 1 of 1
APPLICATION NO. : 11/224813
DATED : July 28, 2009
INVENTOR(S) : Koji Fujiwara et al.

It is certified that error appears in the above-identified patent and that said Letters Patent is hereby corrected as shown below:

Column 20:
Line 15, delete "claim 1," and insert -- claim 11, --.

Signed and Sealed this

Twenty-second Day of September, 2009

David J. Kappos
*Director of the United States Patent and Trademark Office*